(12) United States Patent
Cho et al.

(10) Patent No.: US 7,943,348 B2
(45) Date of Patent: May 17, 2011

(54) METHOD AND APPARATUS FOR AMPLIFYING NUCLEIC ACIDS

(75) Inventors: Yoon-kyoung Cho, Suwon-si (KR); Joon-ho Kim, Seongnam-si (KR); Kak Namkoong, Seoul (KR); Geun-bae Lim, Pohang-si (KR); Jun-hong Min, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 12/504,271

(22) Filed: Jul. 16, 2009

(65) Prior Publication Data

US 2010/0021972 A1    Jan. 28, 2010

Related U.S. Application Data

(62) Division of application No. 11/071,383, filed on Mar. 3, 2005, now Pat. No. 7,579,172.

(30) Foreign Application Priority Data

Mar. 12, 2004  (KR) .................................. 2004-16795

(51) Int. Cl.
*C12Q 1/68* (2006.01)
*C12P 19/34* (2006.01)
(52) U.S. Cl. .......................... 435/91.2; 435/6; 435/91.1
(58) Field of Classification Search .................. None
See application file for complete search history.

(56) References Cited

U.S. PATENT DOCUMENTS

| | | | |
|---|---|---|---|
| 5,939,261 A | | 8/1999 | Loewy et al. |
| 5,958,694 A | | 9/1999 | Nikiforov |
| 7,595,195 B2 * | | 9/2009 | Lee et al. .................... 436/52 |
| 2002/0068357 A1 * | | 6/2002 | Mathies et al. ............ 435/287.2 |

FOREIGN PATENT DOCUMENTS

JP     2003505059 T    2/2003

(Continued)

OTHER PUBLICATIONS

Japanese Office Action for application No. 2005-071485 dated Nov. 27, 2007.

(Continued)

*Primary Examiner* — Young J Kim
(74) *Attorney, Agent, or Firm* — Cantor Colburn LLP

(57) ABSTRACT

A method and apparatus for amplifying nucleic acids. The method includes introducing into a reaction vessel via different inlet channels a reactant aqueous solution containing reactants for nucleic acid amplification and a fluid that is phase-separated from the reactant aqueous solution and does not participate in amplification reaction, creating a plurality of reactant aqueous solution droplets surrounded by the fluid by contacting the reactant aqueous solution with the fluid in the reaction vessel, and amplifying the nucleic acids in the reactant aqueous solution droplets. The apparatus includes a substrate, a reaction vessel formed inside of the substrate, at least one first inlet channel formed inside the substrate, connected to an end of the reaction vessel, and allowing introduction of a reactant aqueous solution containing reactants for nucleic acid amplification into the reaction vessel, a second inlet channel formed inside the substrate, connected to the end of the reaction vessel, and allowing introduction of a fluid that is phase-separated from the reactant aqueous solution and does not participate in amplification reaction into the reaction vessel, and a heating unit installed on the substrate in such a way to thermally contact with the substrate and heating the substrate.

10 Claims, 17 Drawing Sheets

FOREIGN PATENT DOCUMENTS

| | | |
|---|---|---|
| WO | 93/22053 A1 | 11/1993 |
| WO | 01/07159 A2 | 2/2001 |

OTHER PUBLICATIONS

European Search Report: App. No. 05004816.4-EP 05 00 4816; Date of Completion: Jul. 4, 2005.

European Search Report for Application No. EP 05 00 4816; Date of completion of search: Oct. 12, 2005.

Chiou, et al., "A Closed-Cycle Capillary Polymerase Chain Reaction Machine" Analytical Chemistry, vol. 73, No. 9, 2001, pp. 2018-2021.

Handbook of Lectures of the 49th Joint Lecture Meeting of the Applied Physics, vol. 3, 2002, p. 1298.

Kopp, et al., "Chemical Amplification: Continuous-Flow PCR on a Chip", Science, vol. 280, pp. 1046-1048, Dated: May 15, 1998.

Song, et al., "A Microfluidic System for Controlling Reaction Networks in Time", Angew. Chem. Int. Ed. 2003, 42, No. 7, pp. 768-772.

Koenig, et al., "Selective Infection of Human CD4+Cells by Simian Immunodeficiency Virus: Protective Infection Associated With Envelope Glycoprotein-Induced Fusion", Proc. Natl. Acad. Sci. USA, vol. 86, pp. 2443-2447, Dated: Apr. 1989.

Baker, et al., "Single Molecule Amplification in a Continuous Flow Labchip Device", 7th International Conference on Miniaturized Chemical and Biochemical Analysis Systems, pp. 1335-1338, Dated: Oct. 5-9, 2003.

Nakano, et al., "Single-Molecule PCR using Water-in-Oil Emulsion", Journal of Biotechnology 102 (2003) 117-124.

Lagally, et al., "Single-Molecule DNA Amplification and Analysis in an Integrated Microfluidic Device", Analytical Chemistry, vol. 73, No. 3, Dated: Feb. 1, 2001, pp. 565-570.

\* cited by examiner

METHOD AND APPARATUS FOR AMPLIFYING NUCLEIC ACIDS

This application is a divisional application of U.S. application Ser. No. 11/071,383, filed on Mar. 3, 2005 now U.S. Pat. No. 7,579,172, which claims the priority to Korean Patent Application No. 10-2004-0016795, filed on Mar. 12, 2004, in the Korean Intellectual Property Office, the disclosures of which are incorporated herein in their entirety by reference.

BACKGROUND OF THE INVENTION

1. Field of the Invention

The present invention relates to a method and apparatus for amplifying nucleic acids, and more particularly, to a method and apparatus for amplifying trace amounts of nucleic acids to a level necessary for a specific analysis.

2. Description of the Related Art

To disclose the genetic information of nucleic acids such as DNAs and RNAs for the purpose of sequence analysis and disease diagnosis, amplification of trace amounts of nucleic acids to a desired level is required. As nucleic acid amplification techniques well known in ordinary persons skilled in the art, there are a typical isothermal amplification technique, such as ligase chain reaction (LCR), strand-displacement amplification (SDA), nucleic acid sequence-based amplification (NASBA), transcription-mediated amplification (TMA), and loop-mediated isothermal amplification (LAMP), and a non-isothermal amplification technique, such as polymerase chain reaction (PCR) that has been recently mainly used.

Among the amplification techniques, the PCR is performed by repeated cycles of three steps: denaturation, annealing, and extension. In the denaturation step, a double-stranded DNA is separated into two single strands by heating at 90° C. or more. In the annealing step, two primers are each bound to the complementary opposite strands at an annealing temperature of 55 to 65° C. for 30 seconds to several minutes in conventional PCR machines. In the extension step, DNA polymerase initiates extension at the ends of the hybridized primers to obtain DNA double strands. The time required for the extension step varies depending on the concentration of a template DNA, the size of an amplification fragment, and an extension temperature. In the case of using common Thermusaquaticus (Taq) polymerase, the primer extension is performed at 72° C. for 30 seconds to several minutes.

However, with respect to nucleic acid amplification according to the above-described PCR technique, when nucleic acids are present in trace amounts, PCR efficiency may be lowered. For this reason, there arises a problem in that amplification is hardly performed or nonspecific PCR products are often produced.

To solve this problem, Kemp et al. suggested a Nested PCR technique in which a two-step PCR is performed using an outer primer pair and an inner primer pair (David J. Kemp et al., 1989, Proc. Natl. Acad. Sci. Vol. 86, 2423~2427). That is, the Nested PCR technique is a technique that prevents production of nonspecific PCR products by performing a first PCR using the outer primer pair and a second PCR using the inner primer pair. However, if the outer primer pair is not removed prior to initiating the second PCR, there may be a problem in that interaction between the outer primer pair and the inner primer pair must be considered. Furthermore, since cross contamination may occur during opening of a reaction vessel in the interim between the first PCR and the second PCR to insert PCR reactants for the second PCR to the reaction vessel, the Nested PCR technique requires a special attention.

Recently, there has been reported a fast PCR technique starting with a single molecule using a micro device in which a reaction vessel is small (E. T. Lagally et al., 2001, Anal. Chem. 73, 565~570). In this PCR technique, however, nucleic acids may be abnormally adsorbed on a surface of the micro reaction vessel made of silicon or glass, thereby adversely affecting PCR amplification. Furthermore, PCR reactants may be evaporated due to their small volume.

Meanwhile, when PCR temperature reaches below the melting temperature of nucleic acids during the PCR, non-specific PCR products such as primer-dimers may be produced.

To solve this problem, there have been suggested a technique in which common components of PCR amplification, such as DNA polymerase, are not inserted until a first cycle reaches the melting temperature of nucleic acids, and a hot start PCR technique. In detail, there are a method of adding common PCR components after a first cycle reaches the melting temperature of nucleic acids, a method in which a wax bead placed on a reaction solution is melted by heating to form a solidified layer having common PCR components thereon so that the reaction solution is mixed with the common PCR components after a first cycle reaches the melting temperature of nucleic acids, and a method using a Taq DNA polymerase antibody in which while a first cycle reaches the melting temperature of nucleic acids, Taq start antibody is released from Taq DNA polymerase so that the Taq DNA polymerase is activated. However, according to the above methods, there is a burden to add PCR reactants during PCR and cross contamination may occur. Furthermore, in the case of using Taq start antibody, an activation time of 10 minutes or more is normally required.

In PCR technique, the amount of PCR products after n cycles would be theoretically $2^n$-fold of the initial amount of target nucleic acids. The amount of PCR products in an initial PCR step increases logarithmically according to the number of cycles. However, since the annealing efficiency of primers and the synthesis efficiency of DNA double strands are actually not 100%, when the amount of PCR products reaches a predetermined level, there is observed a plateau effect in which an increase rate of PCR products decreases and amplification finally stops. In this regard, it is difficult to deduce the initial amount of target nucleic acids from the amount of PCR products. Conventionally, to quantify the initial amount of target nucleic acids, an internal standard sample is used.

Kopp et al. suggested a continuous-flow PCR on a chip in which a PCR solution flows in a reaction vessel with different temperature areas via a micro channel so that continuous PCR amplification is carried out (Martin U. Kopp et al., 1998, Science, Vol. 280, 1046~1048). Since this PCR technique is not based on heating the entire surfaces of the reaction vessel, the reaction rate is determined by a flow rate, not a heating/cooling rate. However, separate channels for several standard samples are required for quantitative analysis, which increases a chip size. Furthermore, a large number of chips for repeated experiments are required. Amplification of different samples using a single channel may cause a problem such as contamination by DNAs adsorbed on the surface of the channel.

Baker et al. suggested PCR amplification based on fluid movement on a glass chip (Jill Baker et al., 2003, Micro TAS, 1335-1338). According to this PCR technique, the temperature of the glass chip is controlled in such a manner that the entire surface of the glass chip is raised by a heater between channels and is cooled by a cooling water beneath the glass chip. Baker et al. reported that when a fluorescent signal was measured during thermal PCR cycles in a channel filled with a diluted sample, a fluorescent peak was detected on a single molecule. However, accomplishment of this result required an analysis procedure such as removal of a background signal from weak fluorescent signal. Therefore, the analysis procedure of a fluorescent signal is obscure and it is impossible to determine whether a fluorescent peak originates from a single molecule.

Nakano et al. suggested a single molecule PCR technique using water-in-oil emulsion as a reactor (Michihiko Nakano et al., 2003, J. Biotechnology, 102, 117-124). In detail, first, an aqueous solution containing a PCR mixture, oil, and a surfactant are placed in a PCR tube and mixed using a magnetic stirrer bar to obtain the water-in-oil emulsion. Initial several cycles of PCR amplification are performed in small aqueous solution droplets. When the small aqueous solution droplets are united by phase separation of the aqueous solution and the oil by centrifugation, later cycles of PCR amplification proceed. This completes the single molecule PCR suggested by Nakano et al. Generally, when the concentration of template DNAs is very low, hybridization between primers of relatively high concentration occurs more easily, relative to that between the template DNAs and the primers, thereby producing nonspecific PCR products. In this regard, the single molecule PCR technique uses the water-in-oil emulsion as the reactor so that primary PCR amplification occurs in aqueous solution droplets containing high concentration template DNAs. When primers, which are one of reactants in the aqueous solution droplets containing the template DNAs, are completely consumed during initial several cycles of PCR, the aqueous solution droplets containing the template DNAs and another aqueous solution droplets containing no template DNAs are united by centrifugation so that secondary PCR amplification is performed by primers present in the aqueous solution droplets containing no template DNAs. However, this technique has several difficulties in actual applications. For example, use of the magnetic stirrer bar whenever preparing a water-in-oil emulsion for infectious disease diagnosis is inconvenient and increases contamination occurrence. Furthermore, the aqueous solution droplets have different sizes, which may cause a reproducibility problem. Still furthermore, in a case where the concentration of the template DNAs is very low, several repeated experiments are required. In addition, there are disadvantages in that a PCR solution has a large volume of about 50 µl and a quantitative PCR is impossible.

Meanwhile, a traditional PCR shows the qualitative results of amplified DNAs by an electrophoresis at the end-point of the PCR reaction, but has many problems such as inaccuracy of the quantitative detection of DNAs. In this regard, a Real-Time PCR was developed to allow for the quantitative detection of amplified DNAs by detecting the intensity of fluorescent light, which is in proportional to the concentration of the amplified DNAs, using an optical detection system.

However, in the case of performing the quantitative detection of amplified DNAs using a typical Real-Time PCR, there are required three or more repeated experiments using a negative control, a positive control, and at least three standard samples with different concentrations, which requires the use of a large number of reactors. It is impossible to provide such a large number of reactors for a micro PCR chip. To have such a large number of reactors, a larger-sized chip is required.

SUMMARY OF THE INVENTION

The present invention provides a method for amplifying nucleic acids in which a fluid and an aqueous solution containing PCR reactants are injected into a reaction vessel via different inlet channels to form aqueous solution droplets surrounded with the fluid in the reaction vessel, the fluid and the aqueous solution being phase-separated from each other, and amplification of the nucleic acids in the aqueous solution droplets is performed.

The present invention also provides an apparatus for amplifying nucleic acids in which the method for amplifying the nucleic acids is performed.

According to an aspect of the present invention, there is provided a method for amplifying nucleic acids, which includes: introducing into a reaction vessel via different inlet channels a reactant aqueous solution containing reactants for nucleic acid amplification and a fluid that is phase-separated from the reactant aqueous solution and does not participate in amplification reaction, creating a plurality of reactant aqueous solution droplets surrounded by the fluid by contacting the reactant aqueous solution with the fluid in the reaction vessel, and amplifying the nucleic acids in the reactant aqueous solution droplets.

The fluid may be at least one selected from silicon oil, mineral oil, perfluorinated oil, hydrocarbon oil, and vegetable oil.

The operation of amplifying the nucleic acids may be performed by polymerase chain reaction (PCR). The operation of amplifying the nucleic acids may also be performed by ligase chain reaction (LCR), strand-displacement amplification (SDA), nucleic acid sequence-based amplification (NASBA), transcription-mediated amplification (TMA), or loop-mediated isothermal amplification (LAMP).

The operation of amplifying the nucleic acids may be performed by PCR in which the entire surface of a substrate is repeatedly heated and cooled to a predetermined temperature.

The operation of amplifying the nucleic acids may be performed by continuous-flow PCR in which a substrate is heated to have at least two different temperature areas and the reactant aqueous solution droplets alternately and repeatedly pass through the different temperature areas. In this case, the substrate may be heated to have at least two different temperature areas using a plurality of independently controllable heaters.

For real-time PCR, the operation of introducing the reactant aqueous solution and the fluid into the reaction vessel may further include introducing into the reaction vessel at least one aqueous solution of a negative control and a positive control for quantitative assay and a standard sample aqueous solution via respective inlet channels different from the inlet channels for the introduction of the reactant aqueous solution and the fluid, and the operation of creating the reactant aqueous solution droplets may further include creating a plurality of control aqueous solution droplets and a plurality of standard sample aqueous solution droplets by contacting the at least one aqueous solution of the negative control and the positive control and the standard sample aqueous solution with the fluid in the reaction vessel.

For multiplex PCR, in the operation of introducing the reactant aqueous solution and the fluid into the reaction vessel, at least two reactant aqueous solutions containing at least two primers may be introduced into the reaction vessel via respective inlet channels.

For hot start PCR, in the operation of introducing the reactant aqueous solution and the fluid into the reaction vessel, a nucleic acid aqueous solution, a common component containing polymerase and dNTP, and primer set may be introduced into respective inlet channels and mixed before being introduced into the reaction vessel to form the reactant aqueous solution.

For single molecule PCR, the reaction vessel may include two primary reaction channels and a single secondary reaction channel connected to a terminal end of each of the two primary reaction channels, and the operation of introducing the reactant aqueous solution and the fluid into the reaction vessel, the operation of creating the reactant aqueous solution droplets, and the operation of amplifying the nucleic acids may be performed in each of the two primary reaction channels. In this case, after the operation of amplifying the nucleic acids, the method may further include combining the reactant aqueous solution droplets in a starting end of the secondary reaction channel to create a plurality of combined reactant aqueous solution droplets in the secondary reaction channel and amplifying the nucleic acids in the combined reactant aqueous solution droplets.

The reaction vessel may include at least one reaction chamber. In this case, after the operation of amplifying the nucleic acids in the reactant aqueous solution droplets, the method may further include combining the reactant aqueous solution droplets in the reaction chamber and amplifying the nucleic acids in the combined reactant aqueous solution droplets. The operation of combining the reactant aqueous solution droplets may be carried out by centrifugation.

According to another aspect of the present invention, there is provided an apparatus for amplifying nucleic acids, which includes: a substrate; a reaction vessel formed inside of the substrate; at least one first inlet channel formed inside the substrate, connected to an end of the reaction vessel, and allowing introduction of a reactant aqueous solution containing reactants for nucleic acid amplification into the reaction vessel; a second inlet channel formed inside the substrate, connected to the end of the reaction vessel, and allowing introduction of a fluid that is phase-separated from the reactant aqueous solution and does not participate in amplification reaction into the reaction vessel; and a heating unit installed on the substrate in such a way to thermally contact with the substrate and heating the substrate, the reactant aqueous solution contacting with the fluid to create a plurality of reactant aqueous solution droplets surrounded by the fluid in the reaction vessel and the nucleic acids being amplified in the reactant aqueous solution droplets.

The substrate may have a hydrophobic surface property. The substrate may be made of poly(dimethylsiloxane) (PDMS), silicon, silicon dioxide, plastic, or glass. The substrate may include a lower substrate and an upper substrate, and the reaction vessel, the first inlet channel, and the second inlet channel may be formed between the lower substrate and the upper substrate.

For continuous-flow PCR, the reaction vessel may be a serpentine reaction channel, the first inlet channel and the second inlet channel may be connected to a staring end of the reaction channel, and an outlet port for releasing the fluid and an amplification product may be connected to a terminal end of the reaction channel.

The heating unit may be installed at a lower surface of the substrate and include at least two heaters for heating the substrate to allow the substrate to have at least two different temperature areas.

The heating unit may include a plurality of independently controllable heaters installed at a lower surface of the substrate to heat the substrate so that the substrate has at least two temperature areas.

The reaction channel may alternately and repeatedly pass through the temperature areas.

The second inlet channel may linearly extend from the starting end of the reaction channel and the first inlet channel may be formed perpendicularly to the second inlet channel.

For real-time PCR, the apparatus may further include a third inlet channel formed inside the substrate, connected to the end of the reaction channel, and allowing introduction of at least one selected from a negative control aqueous solution and a positive control aqueous solution for quantitative assay into the reaction channel and a fourth inlet channel formed inside the substrate, connected to the end of the reaction channel, and allowing introduction of a standard sample aqueous solution for quantitative assay into the reaction channel.

The fourth inlet channel may be connected to at least two standard sample inlet channels for introduction of standard samples and a distilled water inlet channel for diluting the standard samples to a predetermined concentration. The fourth inlet channel may have a serpentine shape.

For multiplex PCR, the apparatus may include at least two first inlet channels and the first inlet channels may be correspondingly connected to at least two primer inlet channels for introduction of at least two different primers into the first inlet channels. In this case, each of the first inlet channels may have a serpentine shape.

For hot start PCR, the first inlet channel may be connected to a primer inlet channel for introduction of a primer into the first inlet channel and a common component inlet channel for introduction of a common component including polymerase and dNTP into the first inlet channel. In this case, a portion of a starting end side of the reaction channel may have a serpentine shape.

For single molecule PCR, the reaction vessel may include two serpentine primary reaction channels and a single serpentine secondary reaction channel connected to a terminal end of each of the two primary reaction channels, and the first inlet channel and the second inlet channel may be connected to starting ends of the two primary reaction channels. In this case, the heating unit may include a plurality of independently controllable heaters installed at a lower surface of the substrate to provide two temperature areas for each of the two primary reaction channels and the single secondary reaction channel.

The reaction vessel may be a reaction chamber, the first inlet channel and the second inlet channel may be connected to an end of the reaction chamber, and an outlet channel for releasing the fluid and an amplification product may be connected to the other end of the reaction chamber. In this case, the apparatus may include a plurality of reaction chambers, first inlet channels, second inlet channels, and outlet channels. The heating unit may include a single heater installed at a lower surface of the substrate and heating the entire surface of the substrate to a predetermined temperature.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1A:
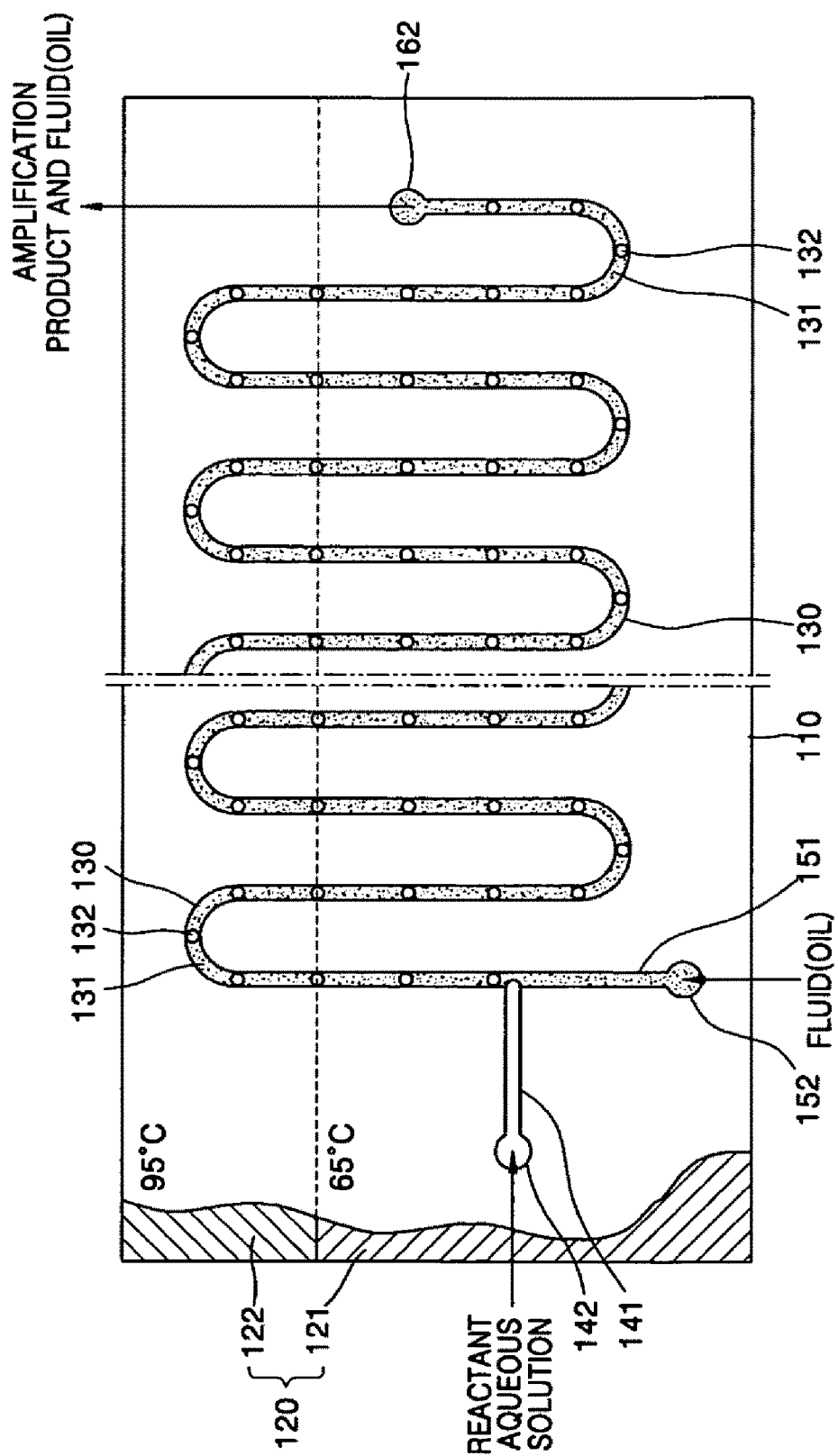
FIG. 1A is a schematic plan view of a nucleic acid amplification apparatus according to a first embodiment of the present invention.

Hereinafter, exemplary embodiments of a method and an apparatus for amplifying nucleic acids according to the present invention will be described in detail with reference to the accompanying drawings. The same reference numerals refer to the same components throughout the drawings.

First Embodiment

Continuous-Flow PCR

Figure 1B:
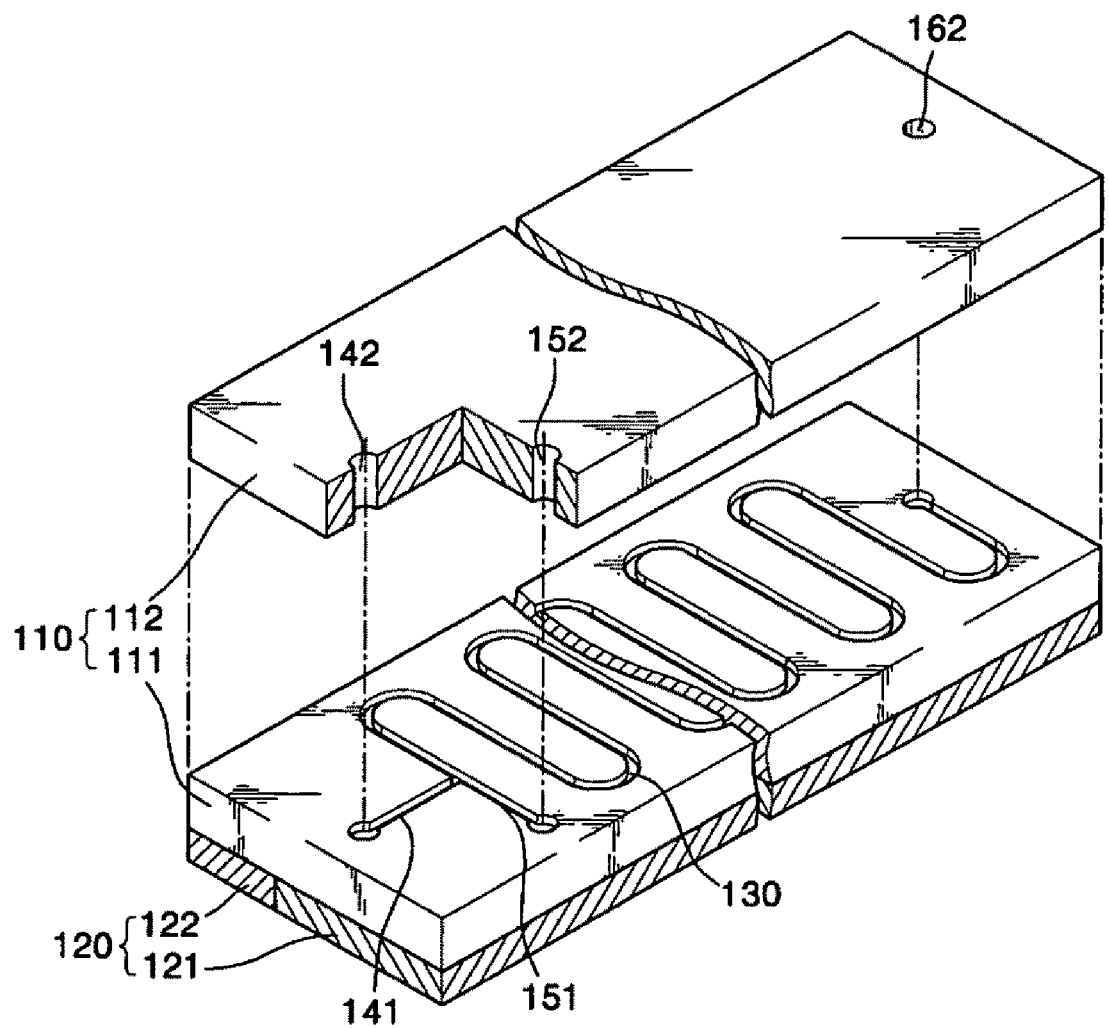
FIG. 1B is an exploded perspective view of the nucleic acid amplification apparatus of FIG. 1A.

FIG. 1A is a schematic plan view of a nucleic acid amplification apparatus according to a first embodiment of the present invention and FIG. 1B is an exploded perspective view of the nucleic acid amplification apparatus of FIG. 1A.

Referring to FIGS. 1A and 1B, the nucleic acid amplification apparatus according to the first embodiment of the present invention includes a substrate 110, a reaction channel 130 formed inside the substrate 110, at least two inlet channels 141 and 151, and a heating unit 120 for heating the substrate 110 to a predetermined temperature.

The substrate 110 may be made of PDMS (Poly Dimethyl Siloxane), silicon, silicon dioxide, plastic, or glass. Preferably, the substrate 110 has a hydrophobic surface property. When the substrate 110 is made of a material having no hydrophobic surface property, it is preferable to modify the surface of the substrate 110 so that the substrate 110 has a hydrophobic surface property. The substrate 110 may include a lower substrate 111 and an upper substrate 112 that are bonded to each other, to form the reaction channel 130 inside the substrate 110. The above-described construction of the substrate 110 may also be applied to all embodiments that will be described hereinafter.

The reaction channel 130 is formed inside the substrate 110 and serves as a reaction vessel in which amplification of nucleic acids occurs. In detail, the reaction channel 130 may have an extended serpentine shape so that it can alternately pass through two areas of the substrate 110 that are maintained at different temperatures, as will be described later.

Among the two inlet channels 141 and 151, a first inlet channel 141 receives an aqueous solution containing reactants for nucleic acid amplification (hereinafter, also simply referred to as "reactant aqueous solution") and a second inlet channel 151 receives a fluid that is phase-separated from the aqueous solution and does not participate in amplification.

Each of the two inlet channels 141 and 151 is connected to a starting end of the reaction channel 130. In detail, the second inlet channel 151 may linearly extend from the starting end of the reaction channel 130. The first inlet channel 141 may be connected to a joint portion between the reaction channel 130 and the second inlet channel 151 so that it can be perpendicular to the second inlet channel 151. That is, the reaction channel 130 and the first and second inlet channels 141 and 151 may be connected in a "T"-shaped form.

The reaction channel 130 and the first and second inlet channels 141 and 151 are formed between the lower substrate 111 and the upper substrate 112. That is, the channels 130, 141, and 151 may be formed to a predetermined depth from the upper surface of the lower substrate 111, as shown in FIG. 1B. Alternatively, the channels 130, 141, and 151 may also be formed in the upper substrate 112. At least one of the channels 130, 141, and 151 may be formed in the lower substrate 111 and the other channels may be formed in the upper channel 112. Preferably, the channels 130, 141, and 151 have a square sectional shape due to easiness of formation, as shown in FIG. 1B. In addition, the channels 130, 141, and 151 may have a polygonal or circular sectional shape.

The first and second inlet channels 141 and 151 are respectively connected to inlet ports 142 and 152 for allowing introduction of the reactant aqueous solution and the fluid from the outside. A terminal end of the reaction channel 130 is connected to an outlet port 162 for releasing amplification products produced by amplification and the fluid. The inlet ports 141 and 142 and the outlet port 162 may be formed in such a way to vertically pass through the upper substrate 112, as shown in FIG. 1B, but are not limited thereto.

The heating unit 120 is installed on a lower surface of the substrate 110 to heat the substrate 110 to a predetermined temperature. The heating unit 120 may be comprised of two heaters 121 and 122 controlled to different temperatures. The heaters 121 and 122 thermally contact with the lower surface of the lower substrate 111 and serve to heat the substrate 110 to two different temperatures. Therefore, the substrate 110 has two areas having different temperatures, for example, a 65° C. area and a 95° C. area. Meanwhile, the heating unit 120 may also be composed of three or more heaters having different temperatures.

A method for amplifying nucleic acids using the above-described nucleic acid amplification apparatus according to the first embodiment of the present invention will now be described.

First, as described above, an aqueous solution containing reactants for nucleic acid amplification and a fluid that is phase-separated from the aqueous solution and does not participate in amplification are inserted into the reaction channel 130 via the first inlet channel 141 and the second inlet channel 151, respectively. At this time, the reactants may include target DNAs, primers, dNTPs, polymerase, and buffers. The aqueous solution is obtained by dissolving these reactants in distilled water. The fluid may be silicon oil, mineral oil, perfluorinated oil, hydrocarbon oil, or vegetable oil.

As described above, when the reactant aqueous solution and the fluid, for example an oil 131, are inserted into the reaction channel 130 via the respective inlet channels 141 and 151 at a constant flow rate, the reactant aqueous solution is surrounded by the oil 131 to form aqueous solution droplets 132. At this time, since the substrate 110 has a hydrophobic surface property as described above, the reactant aqueous solution is surrounded by the oil 131 without being adsorbed to an inner surface of the reaction channel 130, to thereby create the aqueous solution droplets 132.

When a flow rate of the reactant aqueous solution passing through the first inlet channel 141 is controlled, the aqueous solution droplets 132 can be periodically made up to a constant volume in the reaction channel 130.

Here, the aqueous solution droplets 132 surrounded by the oil 131 may be created using a method suggested by Lamagilov et al. [Rustem F. Lamagilov et al., Angew. Chem. Int. Ed. 2003, 42, No. 7, 768-771].

Each of the aqueous solution droplets 132 created as described above serves as a reactor of nucleic acid amplification. That is, nucleic acid amplification occurs in the aqueous solution droplets 132. In detail, the aqueous solution droplets 132 alternately pass through the two temperature areas of the substrate 110 heated by the heaters 121 and 122 during flowing in the reaction channel 130. During this procedure, the reactants for nucleic acid amplification within the aqueous solution droplets 132 undergo repeated heating and cooling. Therefore, repeated cycles of three steps for PCR, i.e., denaturation, annealing, and extension, are performed in the aqueous solution droplets 132. As a result of the above-described continuous-flow PCR, the concentration of amplification products in the aqueous solution droplets 132 gradually increases.

As described above, according to the present invention, since the reactant aqueous solution passes through the first inlet channel 141 with a constant sectional area at a constant flow rate, the aqueous solution droplets 132 created in the reaction channel 130 have a uniform size. Furthermore, several tens to several hundreds of the aqueous solution droplets 132 having a nano-liter (nl) unit volume are easily created, which enables repeated experiments in a relatively small-sized apparatus. Therefore, PCR of about 40 cycles can be performed within a very short time, for example about 10 minutes. In addition, since the aqueous solution droplets 132 are surrounded by the oil 131, a contamination occurrence by adsorption of the reactants for nucleic acid amplification onto the inner surface of the reaction channel 130 can be prevented. At the same time, even when the volume of the reactants is very small, there is no risk of evaporation of the reactants.

Meanwhile, the first embodiment of the present invention has been illustrated that the nucleic acid amplification apparatus includes the two heaters 121 and 122 for heating the substrate 110 to two different temperatures to perform continuous-flow PCR. However, the nucleic acid amplification apparatus according to the first embodiment of the present invention may include only one heater. In this case, a PCR technique in which the entire surface of the substrate 110 is heated or cooled to the same temperature may be performed. Alternatively, typical isothermal amplification techniques such as LCR, SDA, NASBA, TMA, and LAMP, instead of PCR, may be performed. That is, the present invention is not limited to a PCR technique, but can be applied to various nucleic acid amplification techniques.

Second Embodiment

Real-Time PCR

Figure 2:
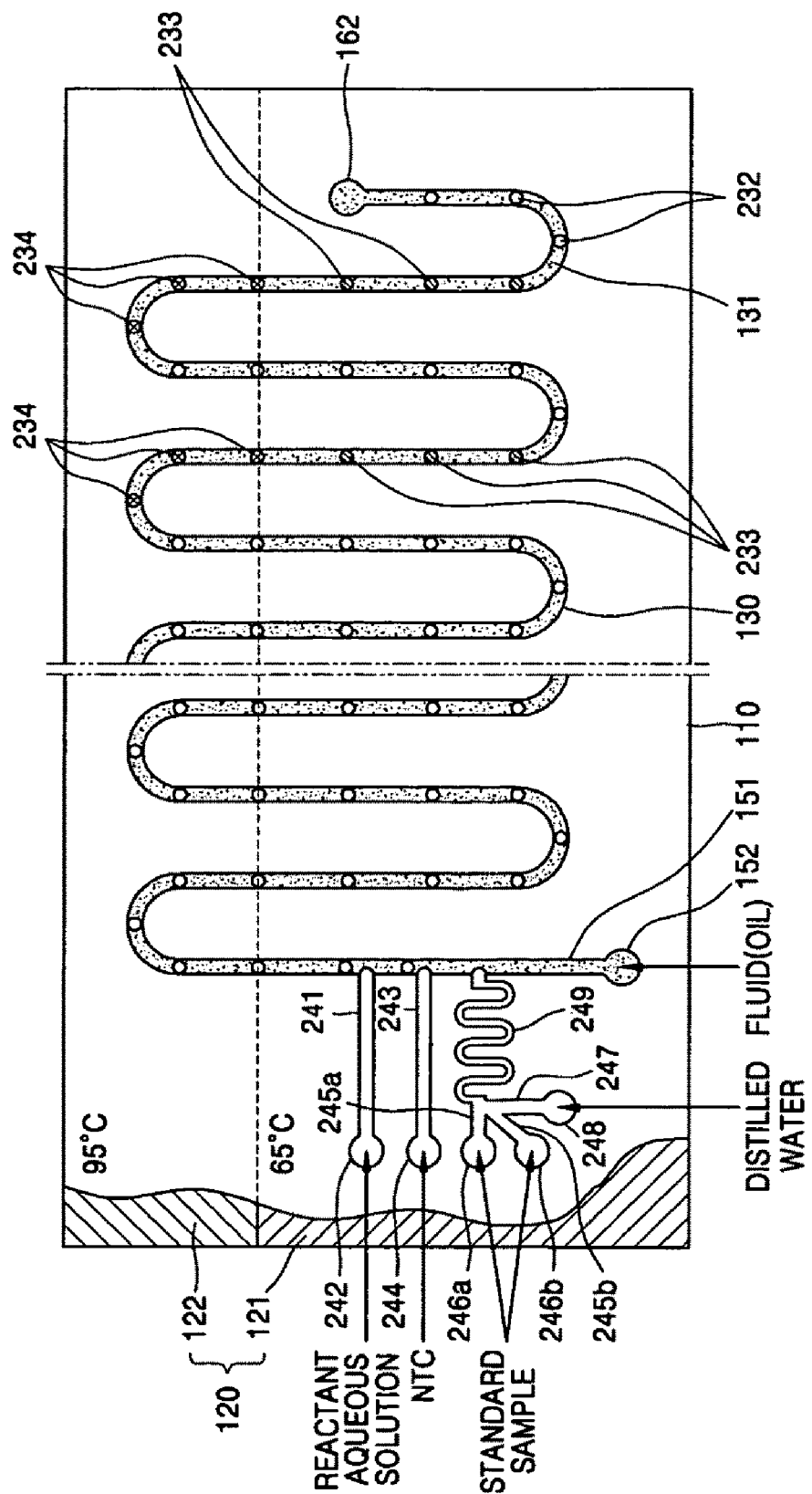
FIG. 2 is a schematic plant view of a nucleic acid amplification apparatus according to a second embodiment of the present invention.
Figure 3:
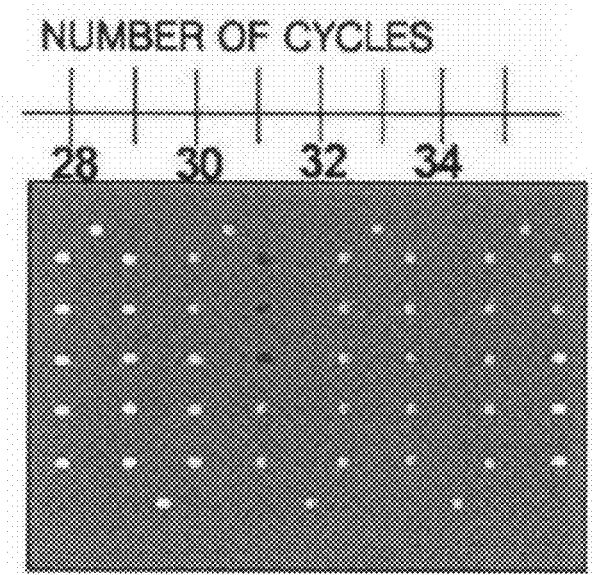
FIGS. 3 and 4 are respectively a charged coupled device (CCD) image of a fluorescent signal emitted from each aqueous solution droplet and an intensity of fluorescent signal versus the number of cycles, when PCR is performed using the nucleic acid amplification apparatus according to the second embodiment of the present invention.
Figure 4:
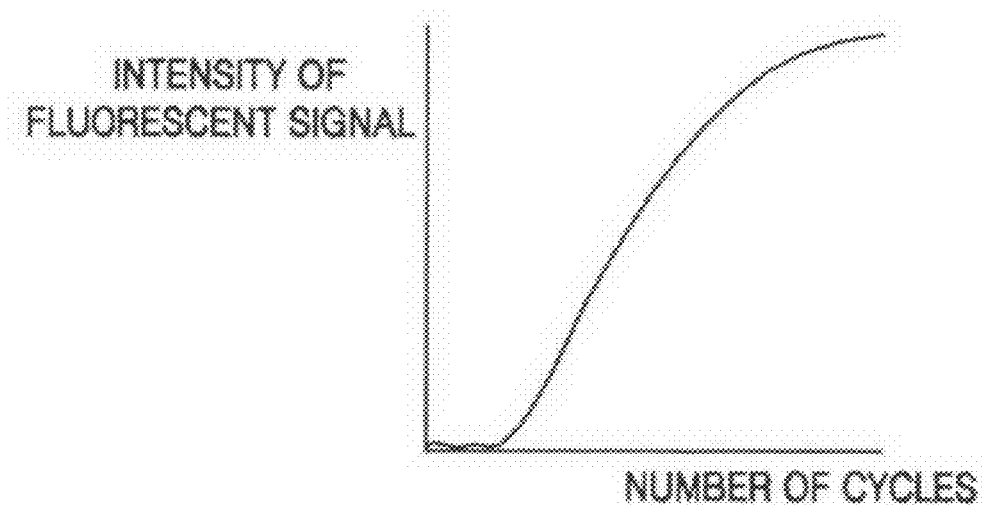

FIG. 2 is a schematic plant view of a nucleic acid amplification apparatus according to a second embodiment of the present invention. FIGS. 3 and 4 are respectively a charged coupled device (CCD) image of a fluorescent signal emitted from each aqueous solution droplet and an intensity of fluorescent signal versus the number of cycles, when PCR is performed using the nucleic acid amplification apparatus according to the second embodiment of the present invention.

First, referring to FIG. 2, the nucleic acid amplification apparatus according to the second embodiment of the present invention includes a substrate 110, a reaction channel formed inside the substrate 110, a plurality of inlet channels 241, 243, 245a, 245b, 247, 249, and 151, and a heating unit 120 for heating the substrate 110 to a predetermined temperature.

Here, the constructions of the substrate 110, the reaction channel 130, and the heating unit 120 are the same as in the first embodiment, and thus, detailed descriptions thereof will be omitted.

The nucleic acid amplification apparatus according to the second embodiment of the present invention has a construction suitable for real-time PCR. For this, the inlet channels 241, 243, 245a, 245b, 247, 249, and 151 are formed inside the substrate 110. In detail, a first inlet channel 241 for introduction of an aqueous solution containing reactants for nucleic acid amplification and a second inlet channel 151 for introduction of the fluid, for example an oil, are connected to a starting end of the reaction channel 130. In addition, a third inlet channel 243 for introduction of a negative control (NTC) aqueous solution and a fourth inlet channel 249 for introduction of a standard sample aqueous solution are also connected to the starting end of the reaction channel 130. Specifically, the second inlet channel 151 may linearly extend from the starting end of the reaction channel 130. The first, third, and fourth inlet channels 241, 243, and 249 may be separated from each other by a predetermined distance and connected perpendicularly to the reaction channel 130. The first inlet channel 241 and the third inlet channel 243 may be respectively connected to inlet ports 242 and 244 that communicate with the outside.

Meanwhile, a positive control, instead of the negative control, may be introduced via the third inlet channel 243. An additional inlet channel for introduction of the positive control may also be formed.

The fourth inlet channel 249 may be connected to two standard sample inlet channels 245a and 245b for introduction of two standard samples and a distilled water inlet channel 247 for introduction of distilled water to dilute the standard samples to a predetermined concentration. The two standard sample inlet channels 245a and 245b and the distilled water inlet channel 247 are respectively connected to inlet ports 246a, 246b, and 248 that communicate with the outside. According to this construction, the standard samples are diluted with the distilled water in the fourth inlet channel 249 to form a standard sample aqueous solution with a predetermined concentration. In this regard, adjustment of the flow rates of the standard samples and the distilled water enables easy formation of the standard sample aqueous solution of different concentrations. At this time, it is preferable to form the fourth inlet channel 249 with a serpentine shape so as to promote sufficient mixing of the standard samples and the distilled water.

In the above-described nucleic acid amplification apparatus according to the second embodiment of the present invention, when the reactant aqueous solution, the NTC aqueous solution, and the standard sample aqueous solution are respectively introduced via the first, third, and fourth inlet channels 241, 243, and 249 while an oil 131 is introduced via the second inlet channel 151, reactant aqueous solution droplets 232 surrounded by the oil 131, NTC aqueous solution droplets 233, and standard sample aqueous solution droplets 234 are created in the reaction channel 130, as described in the first embodiment. At this time, when the aqueous solutions are alternately introduced at a predetermined time interval, the reactant aqueous solution droplets 232, the NTC aqueous solution droplets 233, and the standard sample aqueous solution droplets 234 are alternately created in the reaction channel 130, as shown in FIG. 2. In this way, when the aqueous solution droplets 232, 233, and 234 thus created alternately pass through two temperature areas of the substrate 110 heated by the two heaters 121 and 122 during flowing in the reaction channel 130, continuous-flow PCR is performed in the aqueous solution droplets 232, 233, and 234.

When a fluorescent dye is contained in each of the aqueous solutions, quantitative analysis of nucleic acids is possible by detecting a fluorescent signal emitted from each of the aqueous solution droplets 232, 233, and 234 using an optical detection system. That is, when initially created droplets among the reactant aqueous solution droplets 232 reach a terminal end of the reaction channel 130, a CCD image of a fluorescent signal using a CCD camera as shown in FIG. 3 can be obtained. Referring to FIG. 3, a fluorescent signal is emitted from each of the aqueous solution droplets flowing in a predetermined distance in the reaction channel. Therefore, a more simple and accurate quantitative analysis of fluorescent signals is possible, as compared to a conventional PCR technique in which a fluorescent signal is emitted from the entire surface of a reaction channel. Based on the CCD image thus obtained, a real-time PCR curve as shown in FIG. 4 can be obtained.

As described above, according to the second embodiment of the present invention, a real-time PCR curve can be obtained by one-pot image analysis in a single PCR apparatus, which enables quantitative analysis of nucleic acids. Furthermore, since the reactant aqueous solution, the NTC aqueous solution, and the standard sample aqueous solution are introduced in the single reaction channel 130 and then experiments are performed at the same time, a smaller PCR apparatus can be used and a time required for real-time PCR can be significantly reduced. In addition, since adjustment of the flow rates of the standard samples and the distilled water enables easy formation of the standard sample aqueous solution of different concentrations, more accurate quantitative analysis is possible.

Third Embodiment

Multiplex PCR

Figure 5:
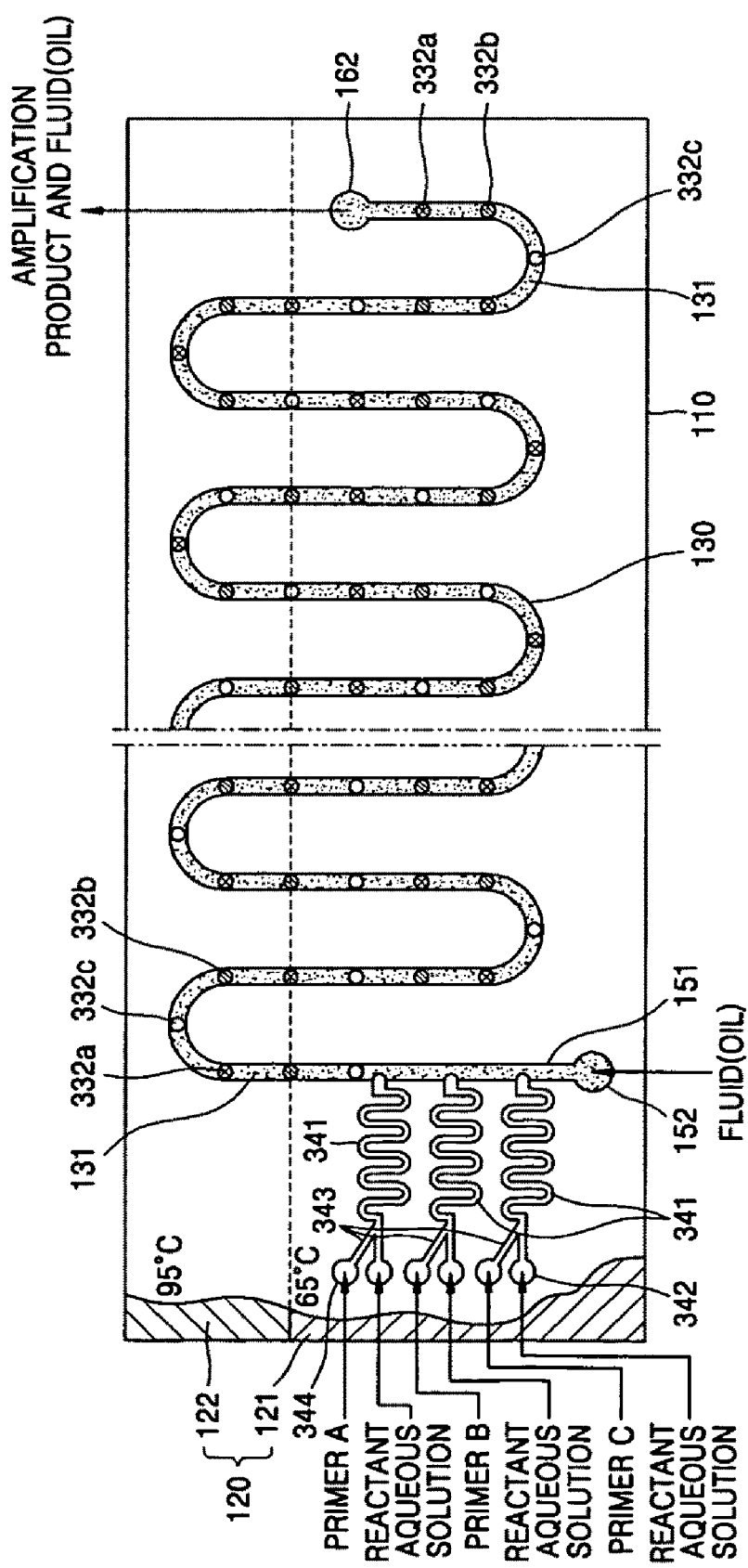
FIG. 5 is a schematic plan view of a nucleic acid amplification apparatus according to a third embodiment of the present invention.

FIG. 5 is a schematic plan view of a nucleic acid amplification apparatus according to a third embodiment of the present invention.

Referring to FIG. 5, in the nucleic acid amplification apparatus according to the third embodiment of the present invention, the constructions of a substrate 110, a reaction channel 130, and a heating unit 120 are the same as in the first embodiment, and thus, detailed descriptions thereof will be omitted.

The nucleic acid amplification apparatus according to the third embodiment of the present invention has a construction suitable for multiplex PCR for simultaneous analysis of multiple genes in a single apparatus. For this, the substrate 110 is formed with a plurality of, for example, three first inlet channels 341 for introduction of reactant aqueous solutions, a plurality of primer inlet channels 343 for introduction of three different primers A, B, and C into the first inlet channels 341, and a single second inlet channel 151 for oil introduction. The second inlet channel 151 may linearly extend from a starting end of the reaction channel 130. The first inlet channels 341 may be separated from each other by a predetermined distance and connected perpendicularly to the reaction channel 130. The primer inlet channels 343 are correspondingly connected to the first inlet channels 341. The first inlet channels 341 and the primer inlet channels 343 may be respectively connected to inlet ports 342 and 344 that communicate with the outside.

In the above-described nucleic acid amplification apparatus according to the third embodiment of the present invention, when the three different primers A, B, and C are introduced into the first inlet channels 341 via the three primer inlet channels 343, respectively, the reactant aqueous solutions in the first inlet channels 341 contain different primers. Preferably, the first inlet channels 341 are formed in a serpentine shape so that the reactant aqueous solutions and the primers are sufficiently mixed.

Next, when the reactant aqueous solutions are introduced into the reaction channel 130 via the first inlet channels 341 while an oil 131 is introduced into the reaction channel 130 via the second inlet channel 151, aqueous solution droplets 332a, 332b, and 332c surrounded by the oil 131 and containing the different primers A, B, and C are created in the reaction channel 130. At this time, when the reactant aqueous solutions containing the different primers A, B, and C are alternately introduced via the first inlet channels 341 at a predetermined time interval, the aqueous solution droplets 332a, 332b, and 332c may be alternately created in the reaction channel 130, as shown in FIG. 5.

As described above, according to the third embodiment of the present invention, it is possible to perform multiplex PCR in which multiple genes are simultaneously analyzed in a single micro-sized apparatus. Furthermore, since the aqueous solution droplets 332a, 332b, and 332c containing different primers are surrounded by the oil 131, cross contamination of the reactant aqueous solutions can be prevented.

Fourth Embodiment

Hot Start PCR

Figure 6:
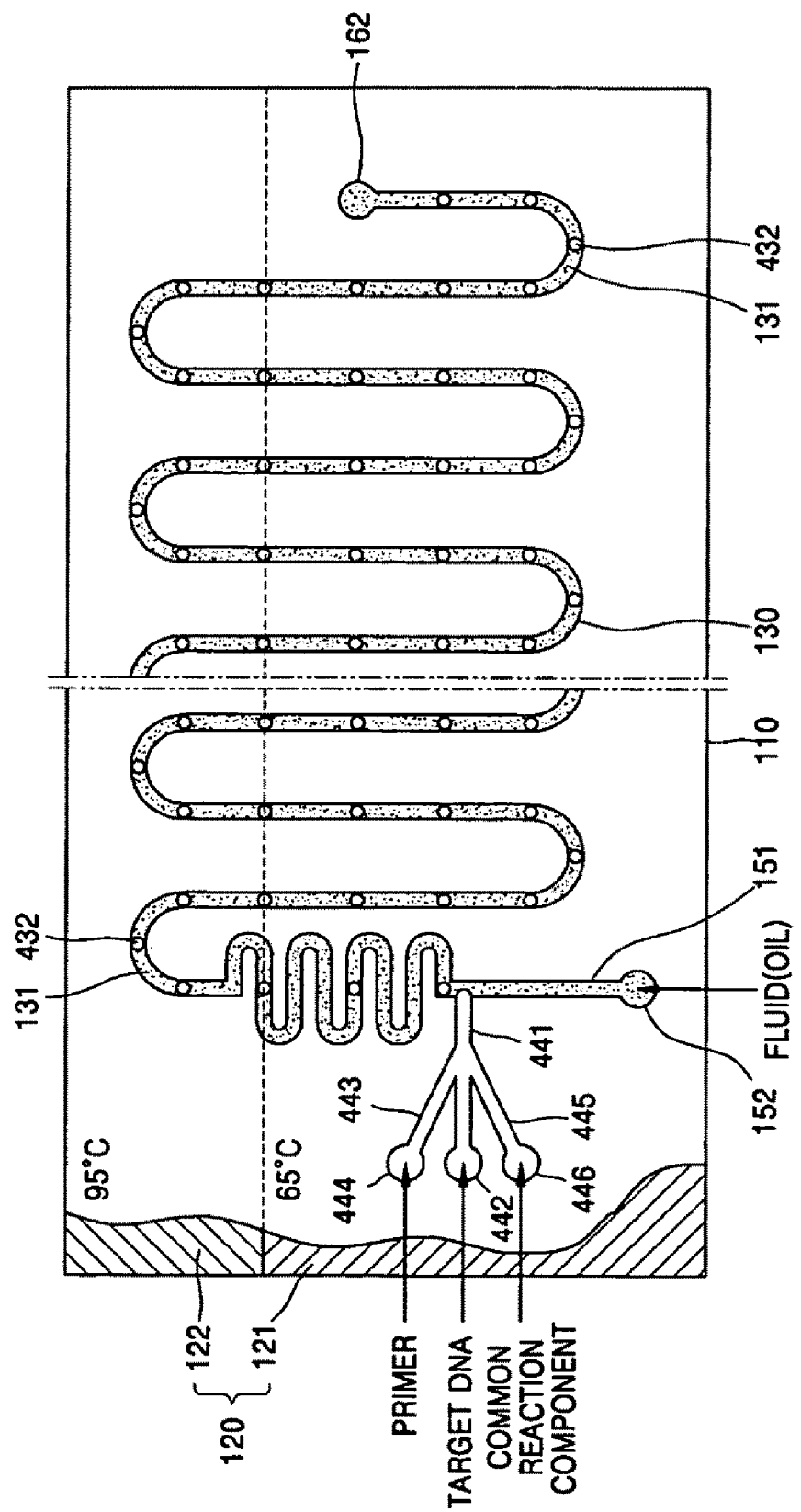
FIG. 6 is a schematic plan view of a nucleic acid amplification apparatus according to a fourth embodiment of the present invention.

FIG. 6 is a schematic plan view of a nucleic acid amplification apparatus according to a fourth embodiment of the present invention.

Referring to FIG. 6, in the nucleic acid amplification apparatus according to the fourth embodiment of the present invention, the constructions of a substrate 110, a reaction channel 130, and a heating unit 120 are the same as in the first embodiment, and thus, detailed descriptions thereof will be omitted.

The nucleic acid amplification apparatus according to the fourth embodiment of the present invention has a construction suitable for hot start PCR. For this, the substrate 110 is formed with a first inlet channel 441 for introduction of a reactant aqueous solution, a primer inlet channel 443 for introduction of primers into the first inlet channel 441, a common component inlet channel for introduction of common reaction components, for example, polymerase, dNTPs, and buffer, into the first inlet channel 441, and a second inlet channel 151 for oil introduction. The second inlet channel 151 may linearly extend from a starting end of the reaction channel 130. The first inlet channel 441 may be connected perpendicularly to the reaction channel 130. The primer inlet channel 443 and the common component inlet channel 445 are connected to a central portion of the first inlet channel 441. The first inlet channel 441, the primer inlet channel 443, and the common component inlet channel 445 may be respectively connected to inlet ports 442, 444, and 446 that communicate with the outside.

In the above-described nucleic acid amplification apparatus according to the fourth embodiment of the present invention, when the primers and the common reaction components are respectively introduced into the primer inlet channel 443 and the common component inlet channel 445 while a target DNA aqueous solution is introduced into the first inlet channel 441, the target DNA aqueous solution, the primers, and the common reaction components are mixed in a central portion of the first inlet channel 441 to form a reactant aqueous solution for nucleic acid amplification. The reactant aqueous solution thus formed is introduced into the reaction channel 130 via the first inlet channel 441. Therefore, a plurality of reactant aqueous solution droplets 432 surrounded by an oil 131 are created in the reaction channel 130. When the reactant aqueous solution droplets 432 alternately pass through two temperature areas of the substrate 110 heated by two heaters 121 and 122 during flowing in the reaction channel 130, continuous-flow PCR is performed in the reactant aqueous solution droplets 432.

Here, it is preferable to form a portion of a starting end side of the reaction channel 130 with a serpentine shape so that the reactants in the aqueous solution droplets 432 are sufficiently heated at a predetermined temperature before the aqueous solution droplets 432 reach a melting temperature of a first cycle.

As described above, according to the fourth embodiment of the present invention, since the target DNA aqueous solution, the primers, and the common components are mixed to form the reactant aqueous solution for nucleic acid amplification immediately before the first cycle of PCR, hot start PCR is possible. Therefore, formation of nonspecific products such as primer-dimer that may be generated at a low temperature prior to initiation of PCR can be prevented.

Fifth Embodiment

Temperature Programmable Continuous-Flow PCR

Figure 7:
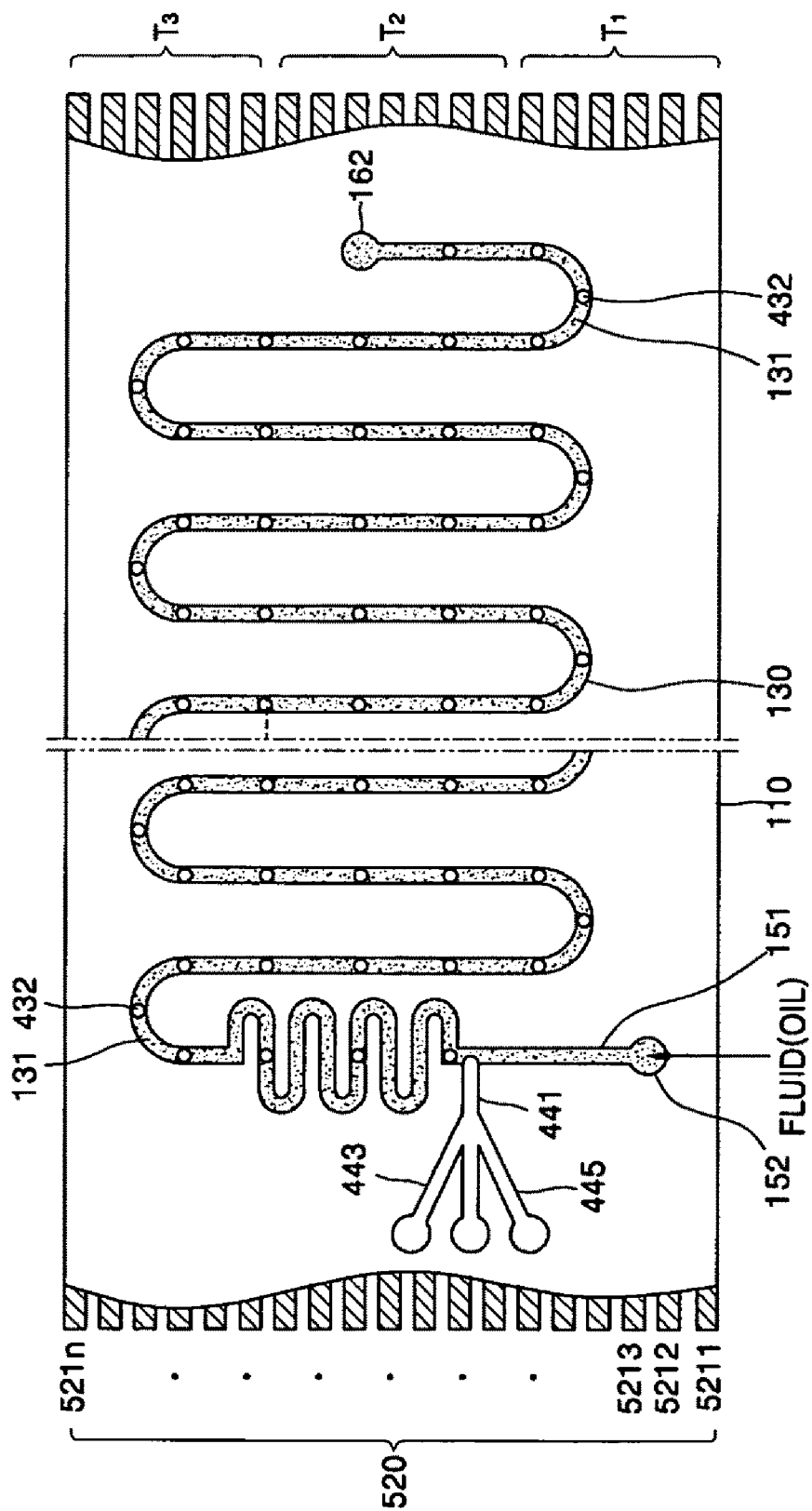
FIG. 7 is a schematic plan view of a nucleic acid amplification apparatus according to a fifth embodiment of the present invention.

FIG. 7 is a schematic plan view of a nucleic acid amplification apparatus according to a fifth embodiment of the present invention.

Referring to FIG. 7, in the nucleic acid amplification apparatus according to the fifth embodiment of the present invention, the constructions of a substrate 110, a reaction channel 130, and inlet channels 441, 443, 445, and 151 are the same as in the fourth embodiment of the present invention, and thus, detailed descriptions thereof will be omitted.

The nucleic acid amplification apparatus according to the fifth embodiment of the present invention includes a heating unit 520 composed of a plurality of independently controllable heaters 5211 through 521$n$. In detail, the heaters 5211 through 521$n$ are disposed in parallel and thermally contact with a lower surface of the substrate 110. The heaters 5211 through 521$n$ serve to heat corresponding portions of the substrate 110 to a predetermined temperature.

Based on the above-described construction, the temperature condition of each of the heaters 5211 through 521$n$ can be changed as necessary, which allows the substrate 110 to have differentially programmed temperature areas. For example, when the heaters 5211 through 521$n$ are divided into three groups that are adjusted to different temperatures, the substrate 110 can have three different temperature areas T1, T2, and T3. Therefore, this embodiment has an advantage in which a nucleic acid amplification experiment can be performed in a single apparatus under different temperature conditions.

The above-described heating unit 520 may also be applied to the nucleic acid amplification apparatuses of the first through fourth embodiments.

Sixth Embodiment

Single Molecule PCR

Figure 8:
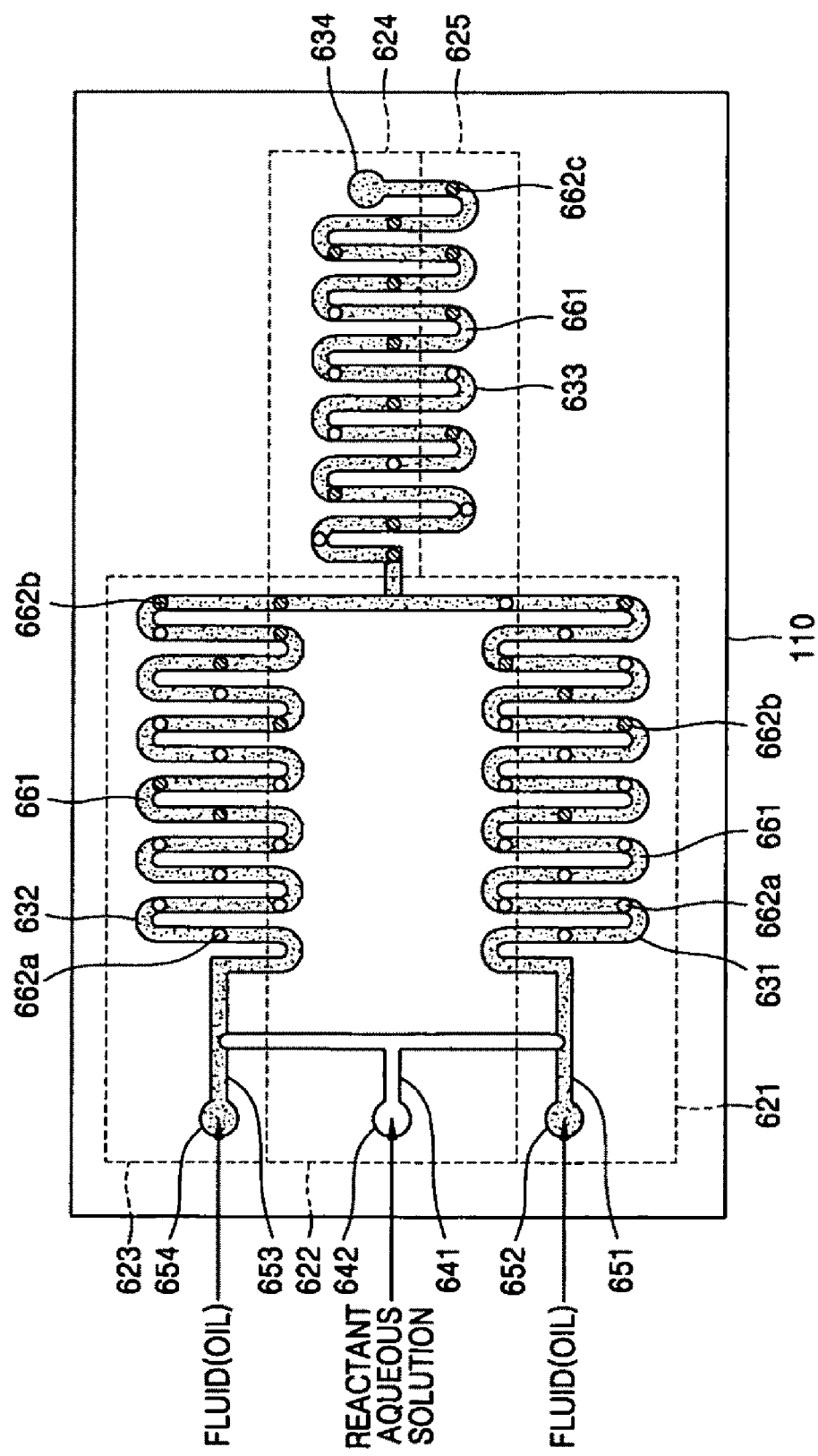
FIG. 8 is a schematic plan view of a nucleic acid amplification apparatus according to a sixth embodiment of the present invention.

FIG. 8 is a schematic plan view of a nucleic acid amplification apparatus according to a sixth embodiment of the present invention.

Referring to FIG. 8, the nucleic acid amplification apparatus according to the sixth embodiment of the present invention has a construction suitable for single molecule PCR. For this, a substrate 110 is formed with two primary reaction channels 631 and 632 for primary PCR, a single secondary reaction channel 633 for secondary PCR, a first inlet channel 641 for introduction of a reactant aqueous solution into the two primary reaction channels 631 and 632, and two second inlet channels 651 and 653 for introduction of an oil into the primary reaction channels 631 and 632, respectively.

The two second inlet channels 651 and 653 are respectively connected to starting ends of the two primary reaction channels 631 and 632. The first inlet channel 641 is commonly connected to the starting ends of the two primary reaction channels 631 and 632. The first inlet channel 641 and the two second inlet channels 651 and 653 may be respectively connected to inlet ports 642, 652, and 654 that communicate with the outside.

Meanwhile, a single second inlet channel may also be commonly connected to the two primary reaction channels 631 and 632. Two first inlet channels may also be correspondingly connected to the two primary reaction channels 631 and 632.

Terminal ends of the two primary reaction channels 631 and 632 are connected to a starting end of the secondary reaction channel 633. A terminal end of the secondary reaction channel 633 is connected to an outlet port 634 that communicates with the outside.

A heating unit is disposed on a lower surface of the substrate 110 to be heated. The heating unit thermally contacts with the lower surface of the substrate 110, as shown in FIG. 8, and may includes a plurality of independently controllable heaters. The heaters thermally contact with corresponding lower surface portions of the substrate 110 to allow the substrate 110 to have a plurality of different temperature areas. For example, as shown in FIG. 8, the heating unit may be composed of five heaters 621 through 625 so that each of the primary reaction channels 631 and 632 and the secondary reaction channel 633 has two different temperature areas.

In the above-described nucleic acid amplification apparatus according to the sixth embodiment of the present invention, aqueous solution droplets 662a and 662b surrounded by an oil 661 are created in the two primary reaction channels 631 and 632. At this time, when the concentration of nucleic acids contained in the reactant aqueous solution is very low, first aqueous solution droplets 662a containing a trace or no concentration of nucleic acids and second aqueous solution droplets 662b containing a relatively high concentration of nucleic acids may be created in the primary reaction channels 631 and 632. While the first and second aqueous solution droplets 662a and 662b flow in the primary reaction channels 631 and 632, primary PCR is performed in the first and second aqueous solution droplets 662a and 662b. During this procedure, most primers in the second aqueous solution droplets 662b containing a relatively high concentration of nucleic acids are consumed. On the other hand, most primers in the first aqueous solution droplets 662a remain unreacted.

The first and second aqueous solution droplets 662a and 662b are combined in the secondary reaction channel 633 after the primary PCR is completed. At this time, the first aqueous solution droplets 662a and the second aqueous solution droplets 662b may be combined among themselves or may form third aqueous solution droplets 662c. In the case of the latter, since nucleic acids of the second aqueous solution droplets 662b meet with primers of the first aqueous solution droplets 662a, the nucleic acids and the primers coexist in the third aqueous solution droplets 662c. Therefore, while the third aqueous solution droplets 662c flow in the secondary reaction channel 633, secondary PCR is performed.

As described above, according to this embodiment of the present invention, two-step PCR is performed in a single apparatus. Therefore, sensitivity of PCR can be remarkably enhanced. Furthermore, since several tens to several hundreds of the aqueous solution droplets 662a and 662b can be continuously created in a single apparatus, trace amounts of nucleic acids can be sufficiently amplified even by only one-pot experiment. In addition, since the aqueous solution droplets 662a, 662b, and 662c used as reactors have a very small volume, sensitivity in amplification of trace amounts of nucleic acids is significantly enhanced.

Meanwhile, the above-described single molecule PCR technique using two-step PCR may also be applied to a nucleic acid amplification apparatus of a chamber shape as will be described later, in addition to the nucleic acid amplification apparatus of a channel shape.

Seventh Embodiment

Single Molecule PCR

Figure 9A:
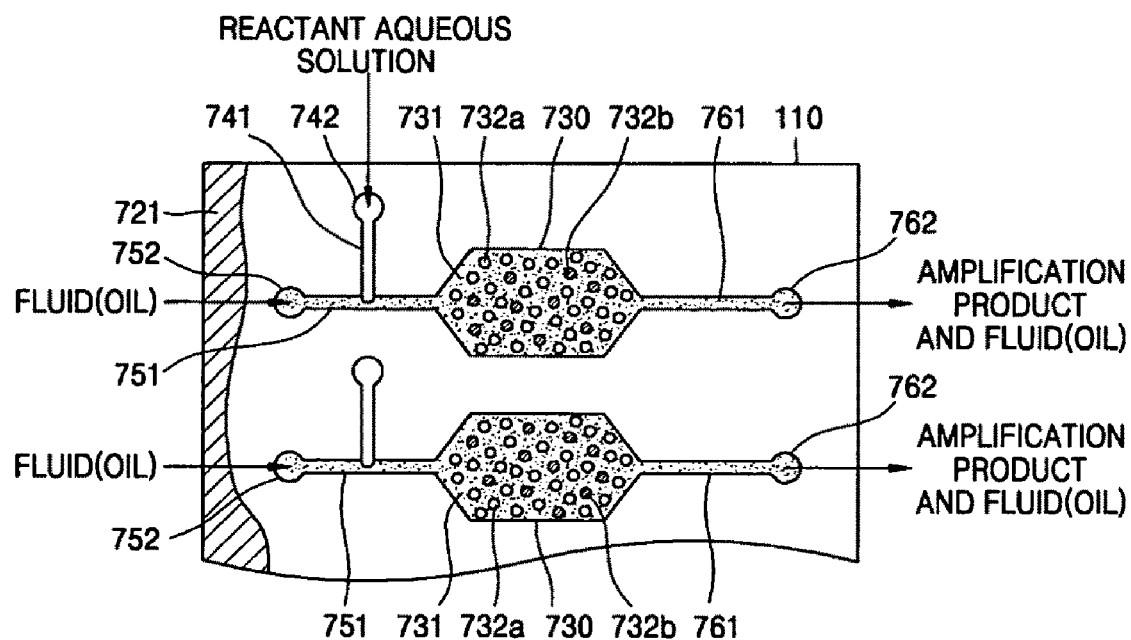
FIGS. 9A and 9B are schematic plan views that illustrate respectively a first PCR step and a second PCR step, in a nucleic acid amplification apparatus according to a seventh embodiment of the present invention.
Figure 9B:
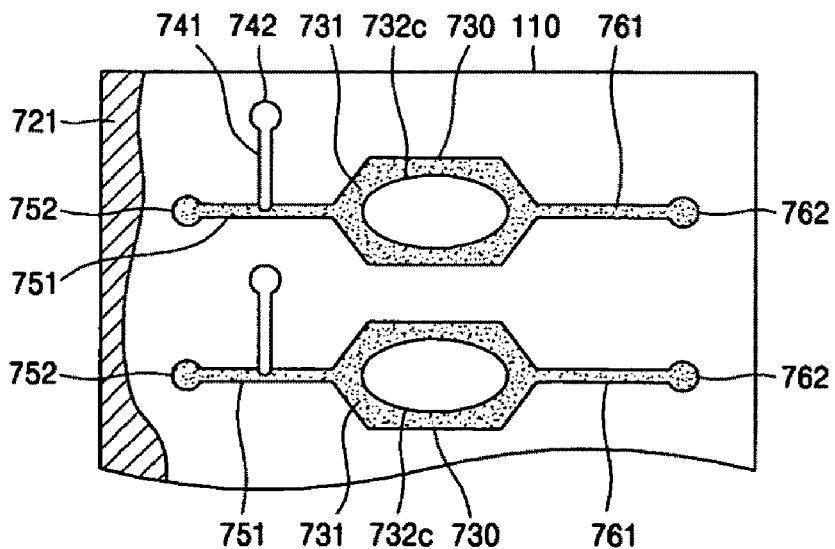

FIGS. 9A and 9B are schematic plan views that illustrate respectively a first PCR step and a second PCR step, in a nucleic acid amplification apparatus according to a seventh embodiment of the present invention.

First, referring to FIG. 9A, the nucleic acid amplification apparatus according to the seventh embodiment of the present invention includes a substrate 110, a reaction chamber 730 formed inside the substrate 110, inlet channels 741 and 751, an outlet channel 761, and a heating unit for heating the substrate 110 to a predetermined temperature.

The construction of the substrate 110 is the same as in the first embodiment.

The reaction chamber 730 is formed inside the substrate 110 and serves as a reaction vessel in which nucleic acid amplification occurs. The reaction chamber 730 may be polygonal or circular and may be formed in several numbers in the single substrate 110.

An end of the reaction chamber 730 is connected to a first inlet channel 741 for introduction of a reactant aqueous solution and a second inlet channel 751 for introduction of a fluid, for example an oil 731. The other end of the reaction chamber 730 is connected to the outlet channel 761 for releasing amplification products and the oil 731 from the reaction chamber 730. The first and second inlet channels 741 and 751 are respectively connected to inlet ports 742 and 752 that communicate with the outside. The outlet channel 761 is connected to an outlet port 762 that communicates with the outside.

The heating unit is disposed on a lower surface of the substrate 110 and includes a heater 721 for heating the substrate 110 to a predetermined temperature.

A method for amplifying nucleic acids using the above-described nucleic acid amplification apparatus according to the seventh embodiment of the present invention will now be described.

First, as described above, the reactant aqueous solution and the fluid, for example, the oil 731 are introduced into the reaction chamber 730 via the first inlet channel 741 and the second inlet channel 751, respectively, to create a plurality of aqueous solution droplets 732a and 732b surrounded by the oil 731 in the reaction chamber 730. At this time, adjustment of the flow rate of the reactant aqueous solution passing through the first inlet channel 741 allows the aqueous solution droplets 732a and 732b created in the reaction chamber 730 to have a uniform volume. During this procedure, when the concentration of nucleic acids contained in the reactant aqueous solution is very low, first aqueous solution droplets 732a containing a trace or no concentration of nucleic acids and second aqueous solution droplets 732b containing a relatively high concentration of nucleic acids can be created in the reaction chamber 730.

Next, when the substrate 110 is periodically heated and cooled by the heater 721, a first PCR step is performed in the aqueous solution droplets 732a and 732b. During the procedure, most primers of the second aqueous solution droplets 732b containing a relatively high concentration of nucleic acids are consumed. On the other hand, most primers of the first aqueous solution droplets 732a remain unreacted.

Referring to FIG. 9B, after the first PCR step is completed, the first aqueous solution droplets 732a and the second aqueous solution droplets 732b are combined by centrifugation to create third aqueous solution droplets 732c with a larger volume. As a result, nucleic acids of the second aqueous solution droplets 732b meet with primers of the first aqueous solution droplets 732a. Therefore, nucleic acids and primers coexist in the third aqueous solution droplets 732c.

In this state, when the substrate 110 is periodically heated and cooled by the heater 721, a second PCR step is performed in the third aqueous solution droplets 732c.

The nucleic acid amplification apparatus according to the seventh embodiment of the present invention has been illustrated in terms of a PCR technique. However, the nucleic acid amplification apparatus according to the seventh embodiment of the present invention may also be applied to typical isothermal amplification techniques such as LCR, SDA, NASBA, TMA, and LAMP.

Experimental Examples

With respect to the continuous-flow PCR according to the first through sixth embodiments of the present invention, since a reactant aqueous solution and an oil, which are different in thermal conductivity, flow in a reaction channel, it is necessary to preset a flow rate of the reactant aqueous solution and the oil. In addition, design parameters such as the thickness of a substrate and a gap between a heater and the reaction channel have to be preset.

Hereinafter, there will be provided parameters required for designing a nucleic acid amplification apparatus, which are determined by simulations based on thermal characteristics of a substrate, and a reactant aqueous solution and an oil flowing in a reaction channel.

Thermal characteristics of several materials are summarized in Table 1 below.

As shown in Table 1, the thermal characteristics of PDMS and perfluorodecalin ($C_{10}F_{18}$) are the worst.

In this regard, the following simulations were performed under the worst conditions using a substrate made of PDMS and perfluorodecalin as an oil.

Experimental Example 1

Two-Dimensional Simulation

Figure 10A:
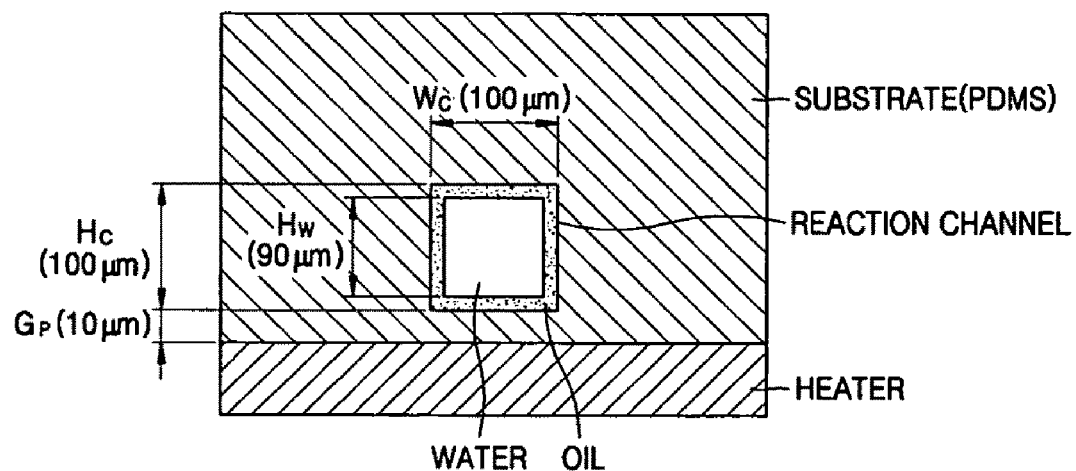
FIGS. 10A and 10B are schematic sectional views of a nucleic acid amplification apparatus for illustrating two-dimensional simulation conditions.
Figure 10B:
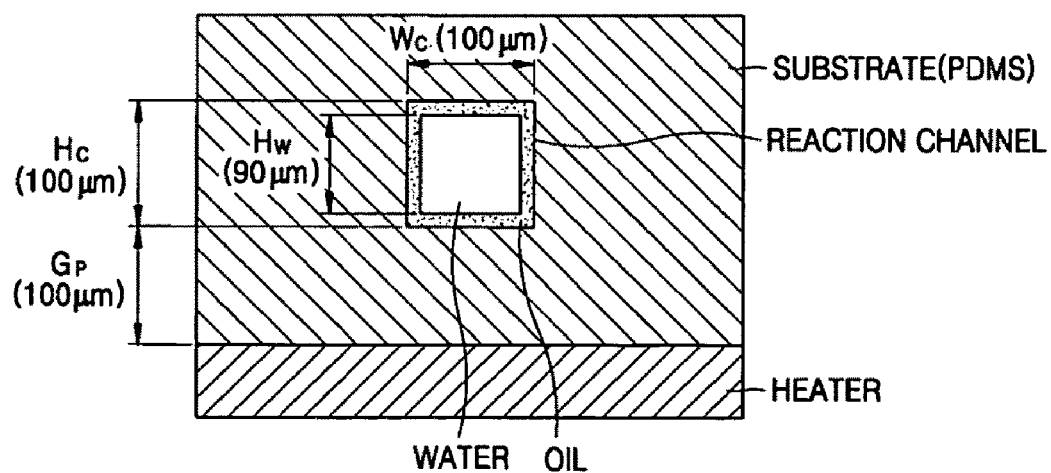

FIGS. 10A and 10B are schematic sectional views of a nucleic acid amplification apparatus for illustrating two-dimensional simulation conditions.

First, referring to FIG. 10A, a substrate was made of PDMS. A heater was disposed on a lower surface of the substrate. The substrate was formed with a reaction channel in which each of a width $W_C$ and a height $H_C$ was 100 µm. A thickness $G_P$ of the substrate between the reaction channel and the heater was set to 10 µm and a height $H_W$ of water in the reaction channel was set to 90 µm.

A first two-dimensional simulation was performed under the above-described conditions.

Then, a second two-dimensional simulation was performed with varying the aspect ratio ($W_C/H_C$) of the reaction channel and a ratio of $H_w$ to $H_C$.

Next, referring to FIG. 10B, a third two-dimensional simulation was performed in the same manner as shown in FIG. 10A except that the thickness $G_P$ of the substrate between the reaction channel and the heater was set to 100 µm.

Meanwhile, the sectional shape of water in the reaction channel will substantially approximate to a circular shape due to the surface tension of water. However, to more easily perform the simulations, it was supposed that water in the reaction channel of FIGS. 10A and 10B had a square sectional shape.

Illustrative conditions of the two-dimensional simulations are summarized in Table 2 below.

TABLE 1

| Material | Thermal conductivity (W/m · K) | Density (kg/m³) | Specific heat (J/kg · k) | Thermal diffusivity (m²/s) | Rank | Kinematic viscosity (m²/s) |
|---|---|---|---|---|---|---|
| Si | 157 | 2329 | 700 | 9.630E−05 | 1 | |
| Glass | 1.13 | 2520 | 753 | 5.955E−07 | 5 | |
| Polycarbonate | 0.2 | 1200 | 1250 | 1.333E−07 | 7 | |
| Thermally Conductive LCP | 20 | 1700 | 900 | 1.307E−05 | 3 | |
| Water | 0.613 | 997 | 4179 | 1.471E−07 | 6 | 1.000E−06 |
| SiO₂ | 10.4 | 2650 | 745 | 5.268E−06 | 4 | |
| Pt | 71.6 | 21500 | 133 | 2.504E−05 | 2 | |
| Perfluorodecalin ($C_{10}F_{18}$) | 0.0677 | 1930 | 970 | 3.613E−08 | 9 | 2.94−E−06 |
| PDMS | 0.17 | 1050 | 1315 | 1.231E−07 | 8 | |

LCP: Liquid crystal polymer, PDMS: Poly(dimethylsiloxane)

TABLE 2

| Section | Thickness of substrate between channel and heater ($G_P$) | Aspect ratio of channel ($W_C/H_C$) | Ratio of water height to channel height ($H_W/H_C$) | Temperature Condition Cooling | Temperature Condition Heating |
|---|---|---|---|---|---|
| ① | 10 μm | 1(100/100) | 0.5 | 95° C. => 60° C. | 30° C. => 95° C. |
| ② | | | 0.8 | | |
| ③ | | | 0.9 | | |
| ④ | | 2(140/70) | 0.8 | | |
| ⑤ | | | 0.9 | | |
| ⑥ | | 4(200/50) | 0.8 | | |
| ⑦ | | | 0.9 | | |
| ⑧ | 100 μm | 1(100/100) | 0.9 | | |

FIGS. 11 through 15 show results of the two-dimensional simulations.

Figure 11:
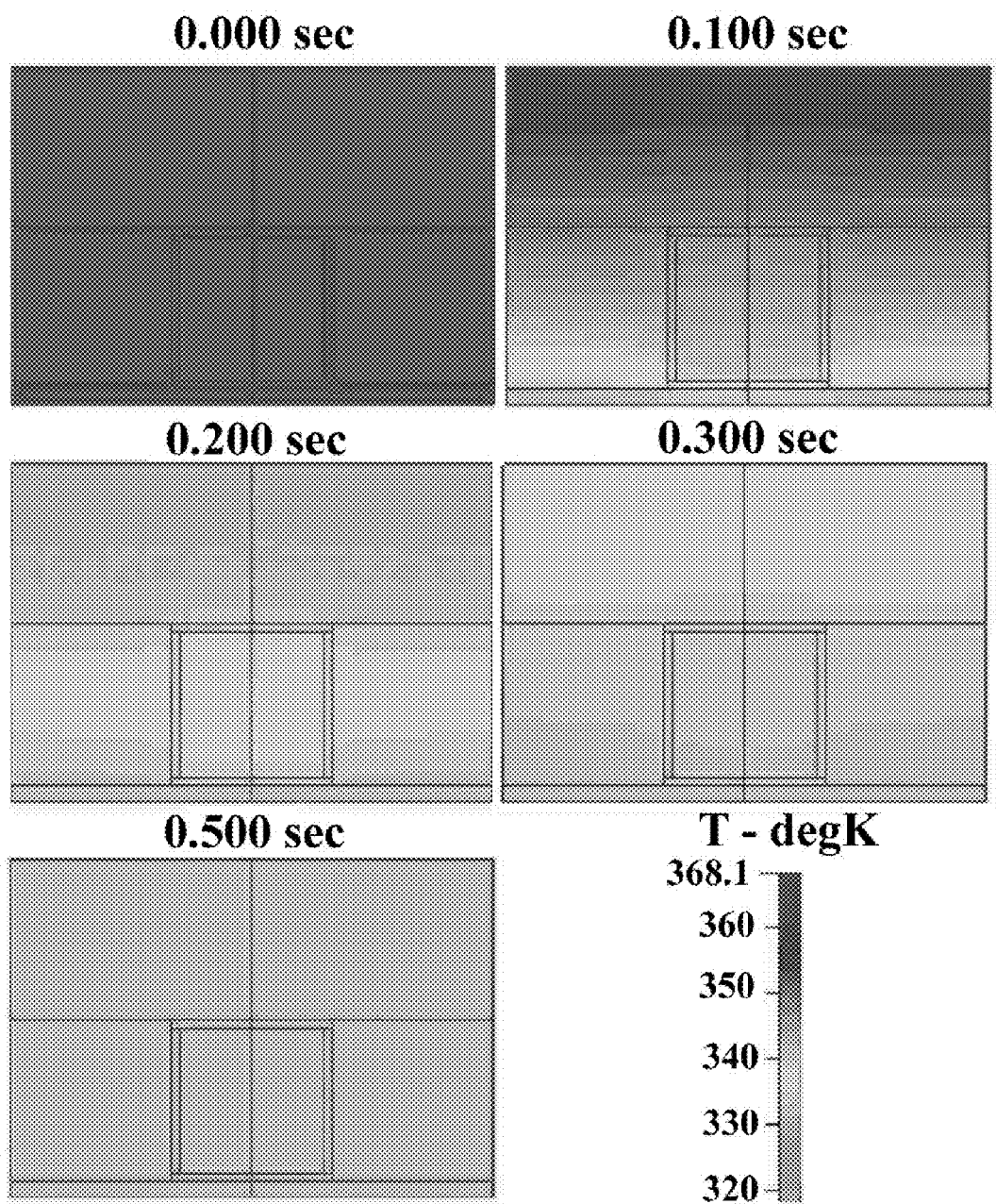
FIG. 11 is a view that illustrates a temperature profile versus time when cooling is performed from 95° C. to 60° C. during the two-dimensional simulation according to the simulation conditions of FIG. 10A.

FIG. 11 illustrates a temperature profile versus time when cooling is performed from 95° C. to 60° C. during the two-dimensional simulation according to the simulation conditions of FIG. 10A.

As shown in FIG. 11, all areas of the nucleic acid amplification apparatus, i.e., the substrate, and the oil and the water contained in the reaction channel reached a target temperature within 0.5 seconds.

Figure 12:
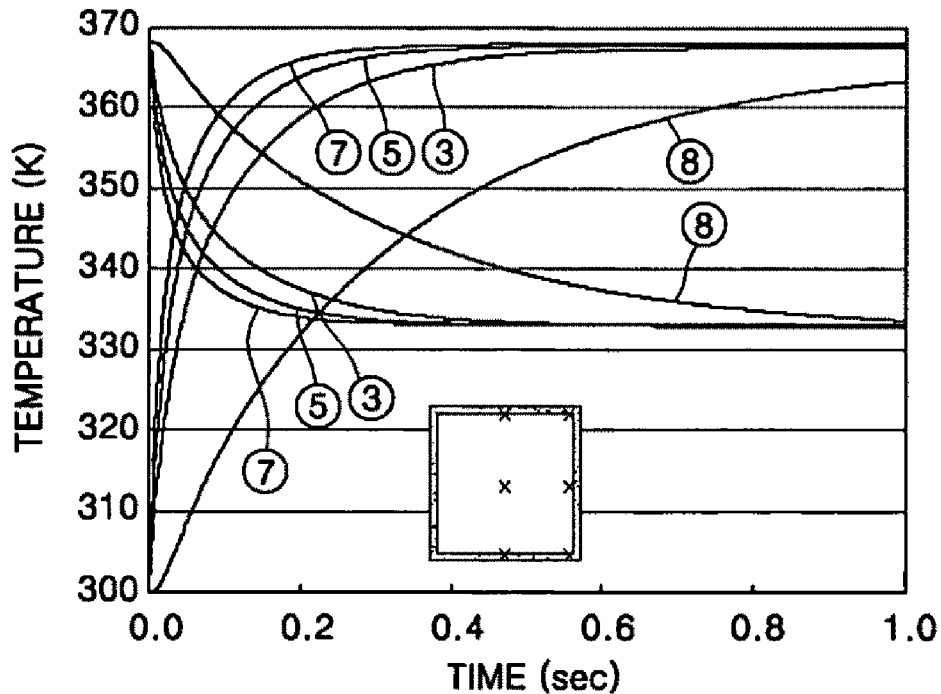
FIG. 12 is a graph that illustrates a change in water temperature versus time in a two-dimensional simulation according to the conditions presented in Table 2.

FIG. 12 is a graph that illustrates a change in water temperature versus time in the two-dimensional simulations according to the conditions presented in Table 2. Each temperature curve of FIG. 12 represents an average value of temperatures of six spots of a water-containing section of the reaction channel with respect to time.

As shown in the graph of FIG. 12, when the thickness $G_P$ of the substrate between the reaction channel and the heater was 10 μm, water temperature reached a target value within 0.5 seconds by cooling and heating regardless of the aspect ratio of the reaction channel.

Meanwhile, as shown in FIG. 12, a temperature change value between heating and cooling is different. In this regard, a graph of FIG. 13 shows a temperature change value normalized by total temperature change value with respect to time.

Figure 13:
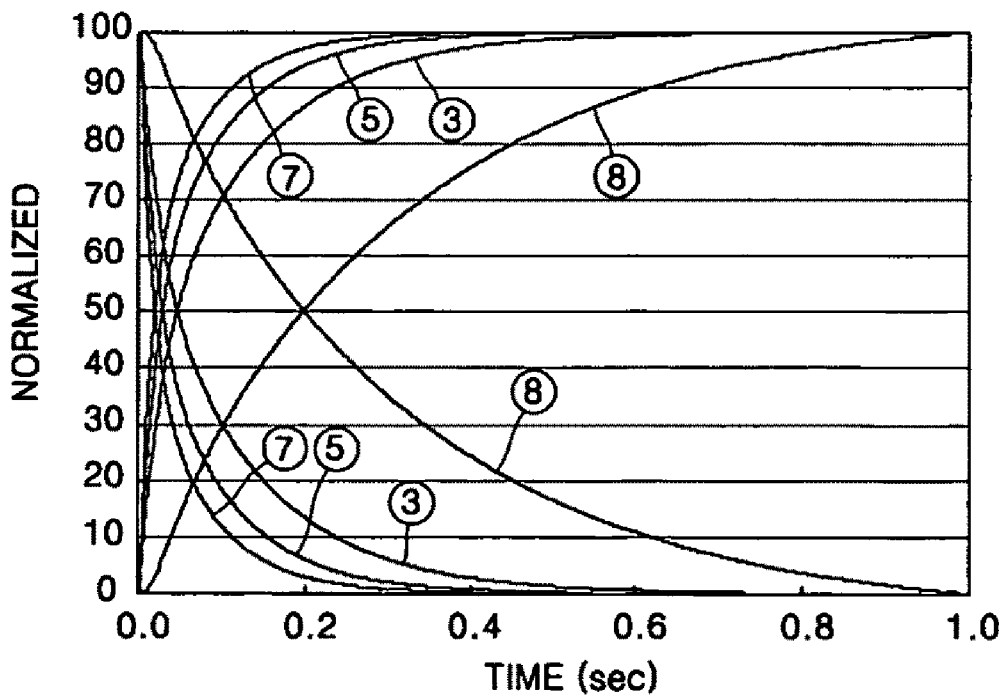
FIG. 13 is a graph that illustrates the temperature change values of the graph of FIG. 12 normalized by a total temperature change value with respect to time.

It can be seen from the graph of FIG. 13 that a change in temperature versus time during heating is similar to that during cooling.

The above simulation results show that a method and an apparatus for amplifying nucleic acids according to the present invention provide a remarkably rapid response speed with respect to temperature change, which ensures rapid PCR.

According to the present invention, in temperature change of water droplets surrounded by oil, temperature uniformity acts as an important factor. The above-described simulations demonstrated that an apparatus and a method for amplifying nucleic acids of the present invention provide temperature uniformity.

Figure 14:
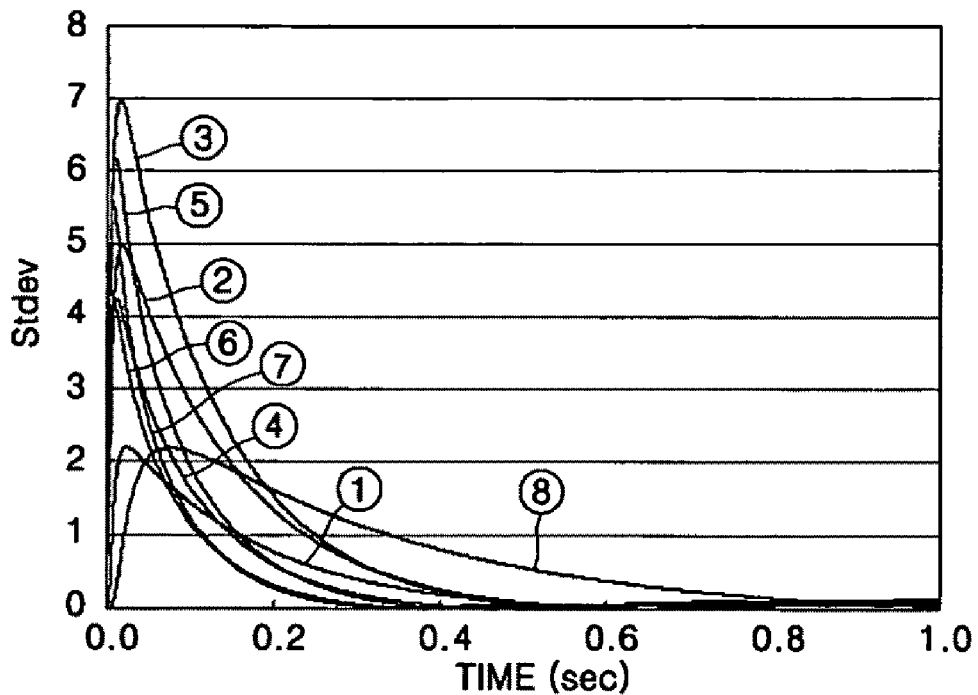
FIG. 14 is a graph that illustrates a standard deviation of water temperature versus time in a two-dimensional simulation according to the conditions presented in Table 2.

FIG. 14 is a graph that illustrates a standard deviation of water temperature versus time in the two-dimensional simulations according to the conditions presented in Table 2. Each standard deviation curve of FIG. 14 represents an average value of standard deviations of temperatures of six spots of a water-containing section of the reaction channel with respect to time.

As shown in the graph of FIG. 14, when the thickness ($G_P$) of the substrate between the reaction channel and the heater was 10 μm, a time for which standard deviation reached 1° C. or less was 0.3 seconds or less regardless of the aspect ratio of the reaction channel. When the thickness ($G_P$) of the substrate between the reaction channel and the heater was 100 μm, standard deviation reached 1° C. or less within 0.4 seconds.

Figure 15:
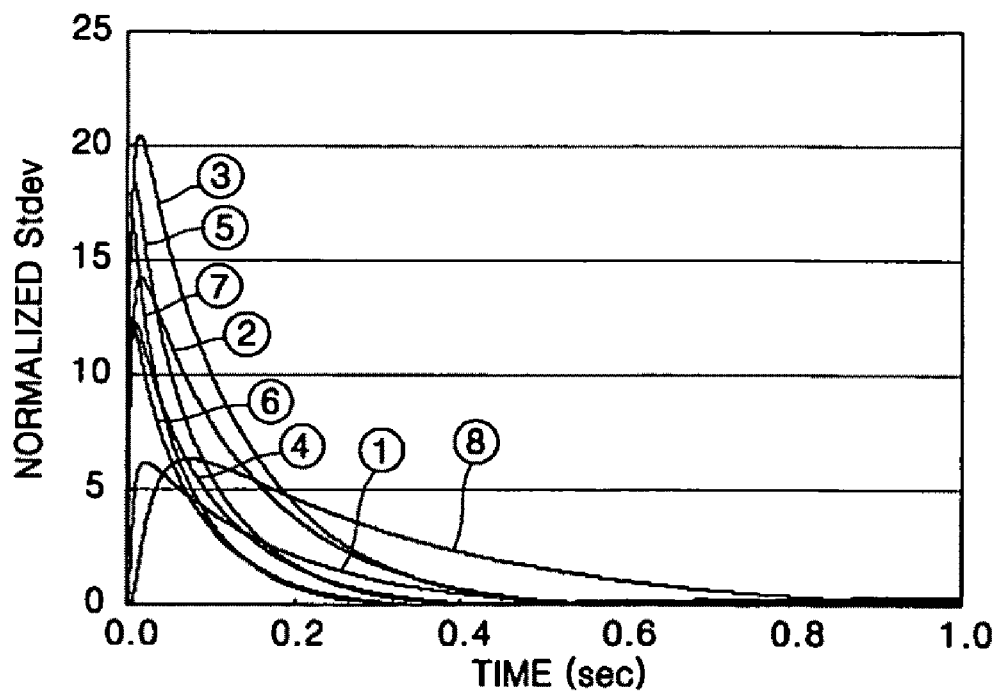
FIG. 15 is a graph that illustrates a ratio of the standard deviation of water temperature of the graph of FIG. 14 with respect to the total temperature change value.

A graph of FIG. 15 shows a ratio of the standard deviation of FIG. 14 to a total temperature change value.

As shown in the graph of FIG. 15, a time required for accomplishing temperature uniformity of 2% or less of total temperature change value was 0.5 seconds or less. This means that when a temperature change of 50° C. occurs, a period of time sufficient to accomplish temperature uniformity of 1° C. or less is 0.5 seconds.

Experimental Example 2

Three-Dimensional Simulation

This Experimental Example was performed to evaluate thermal characteristics of a three-dimensional structure that approximates to an actual structure, based on the above-described two-dimensional simulations.

Figure 16:
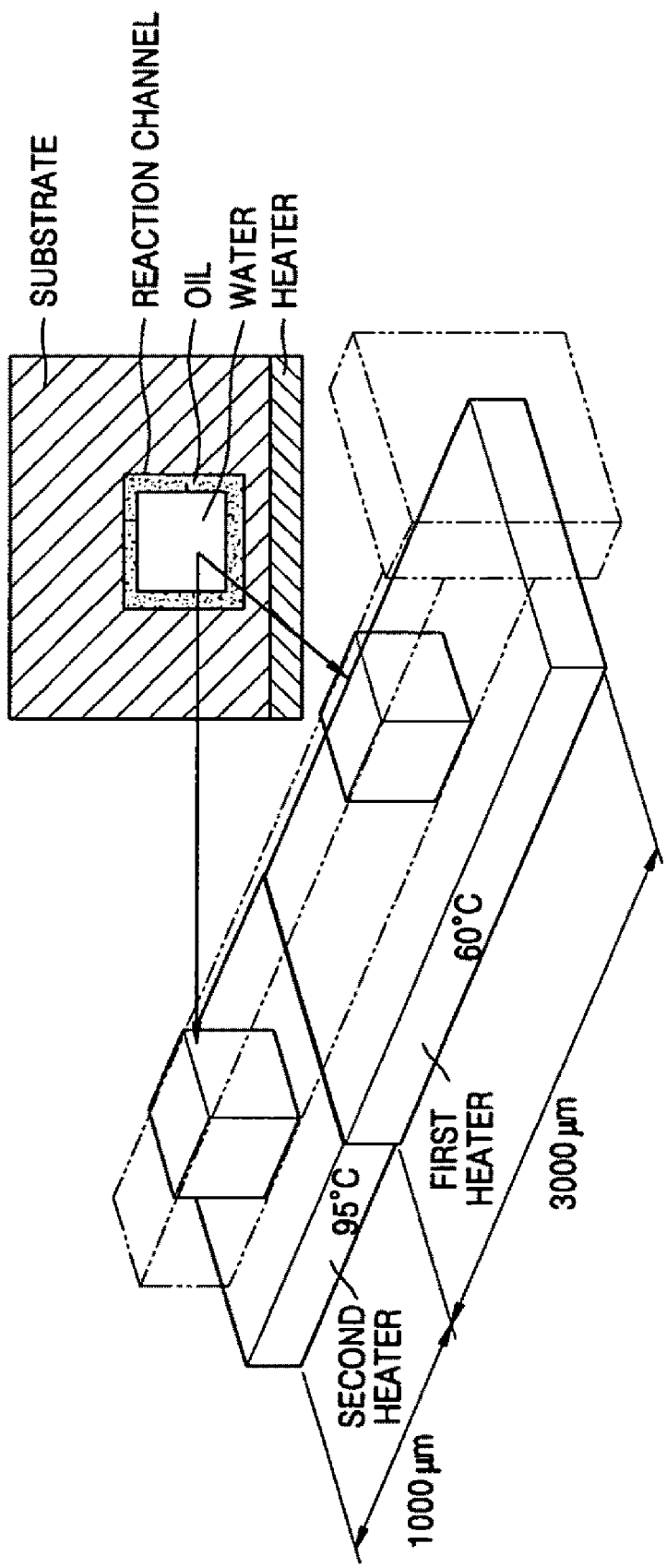
FIG. 16 is a schematic view that illustrates an amplification apparatus for three-dimensional simulation.

FIG. 16 is a schematic view that illustrates an amplification apparatus for three-dimensional simulation.

Referring to FIG. 16, two heaters are disposed on a lower surface of a substrate made of PDMS. The substrate is formed with a reaction channel. A water droplet surrounded by oil is present in the reaction channel.

Under this construction, illustrative conditions for three-dimensional simulation was the same as that as shown in FIG. 10A. That is, each of width $W_C$ and height $H_C$ of the reaction channel was set to 100 μm and a thickness $G_P$ of the substrate between the reaction channel and the heaters was set to 10 μm. Each of the height, width, and the length of the water droplet was set to 90 μm. A length of a first heater was 3,000 μm and a length of a second heater was 1,000 μm.

An initial condition of the three-dimensional simulation was as follows. A temperature of the first heater shown in a right side of FIG. 16 was 60° C. and an initial temperature of oil and water droplet in a first heater area was 95° C. A temperature of the second heater shown in a left side of FIG. 16 was 95° C. and an initial temperature of oil and water droplet in a second heater area was 60° C. In this regard, the first heater area is an area in which oil and water are cooled from 95° C. to 60° C. and the second heater area is an area in which oil and water are heated from 60° C. to 95° C.

FIGS. 17 through 21 show results of the three-dimensional simulation.

Figure 17:
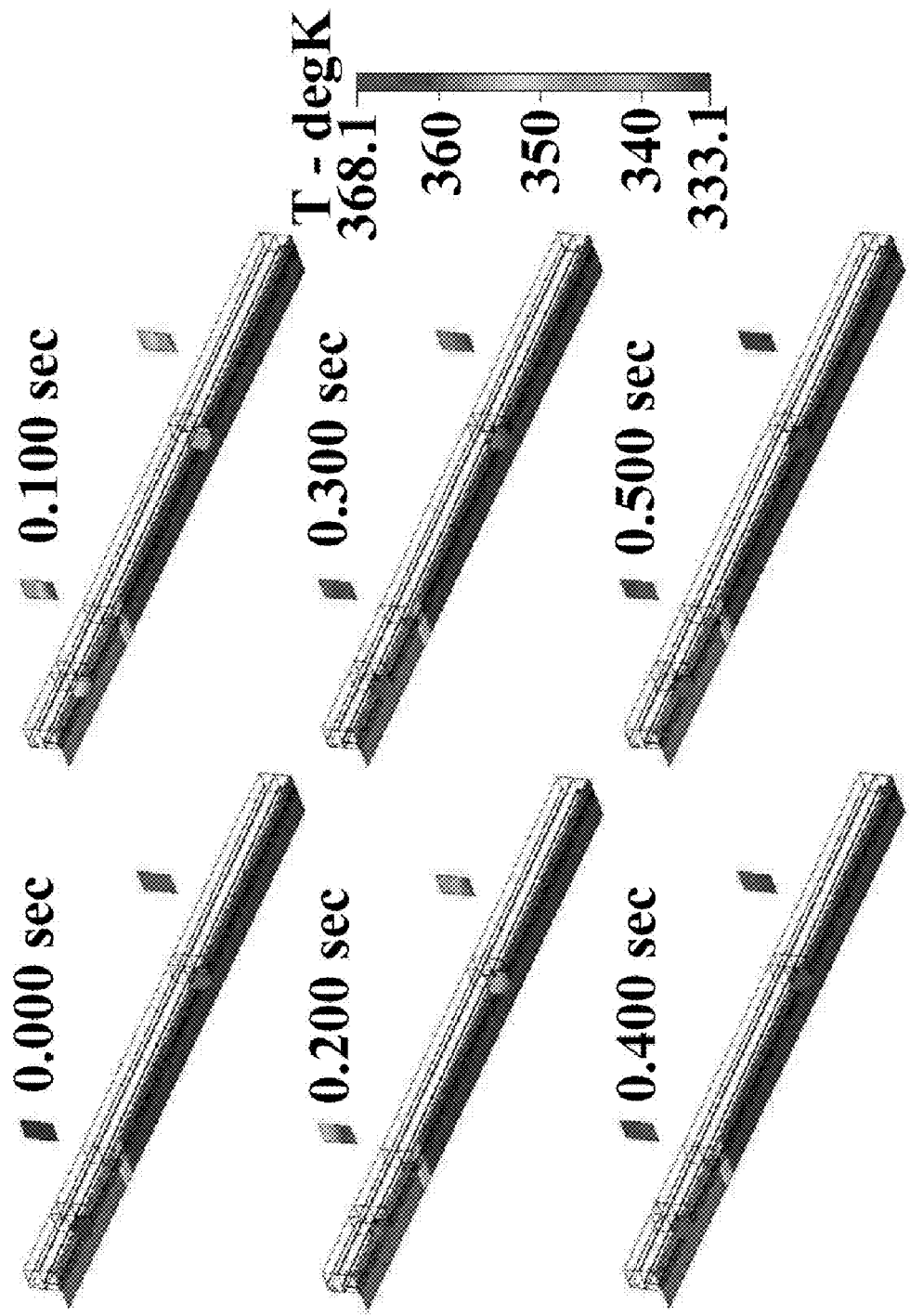
FIG. 17 is a view that illustrates a temperature profile of heater areas of the amplification apparatus versus time when a three-dimensional simulation is performed according to the conditions shown in FIG. 16.

FIG. 17 illustrates a temperature profile of each area of a nucleic acid amplification apparatus with respect to time when three-dimensional simulation is performed according to the conditions shown in FIG. 16

As shown in FIG. 17, all areas of the nucleic acid amplification apparatus reached a target temperature within 0.5 seconds.

Figure 19:
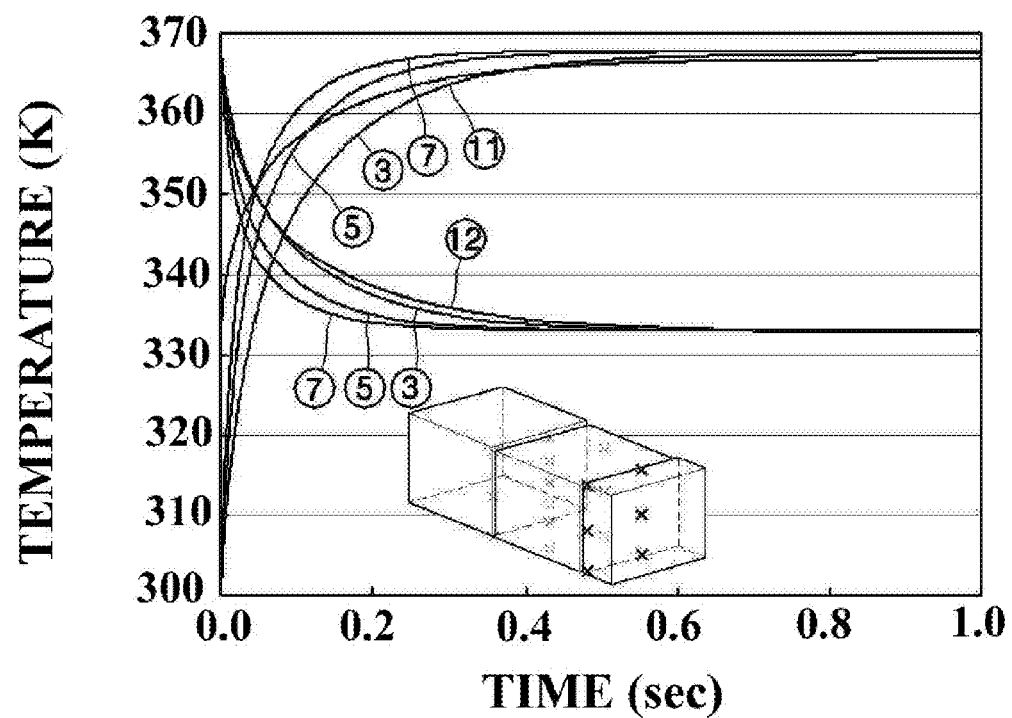
FIG. 19 is a graph that illustrates a change in water temperature versus time when a three-dimensional simulation is performed according to the condition shown in FIG. 16.
Figure 20:
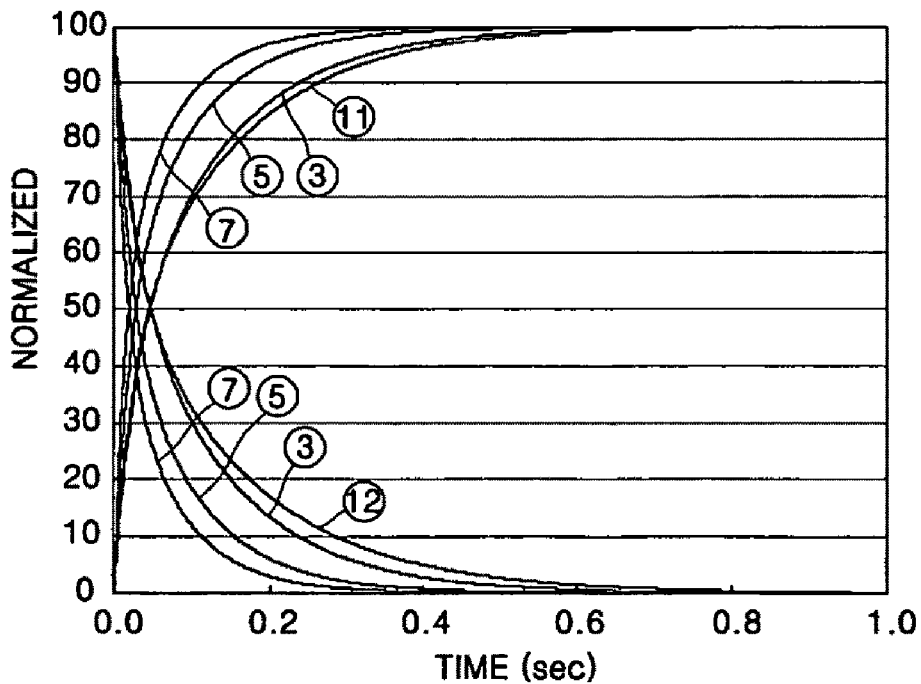
FIG. 20 is a graph that illustrates the temperature change values of the graph of FIG. 19 normalized by a total temperature change value with respect to time.

FIG. 19 is a graph that illustrates a change in water temperature versus time in the three-dimensional simulation performed according to the condition shown in FIG. 16. Each temperature curve of FIG. 19 represents an average value of temperatures of 18 water-containing spots of a reaction channel with respect to time. FIG. 20 is a graph that illustrates the temperature change value of FIG. 19 normalized by a total temperature change value with respect to time.

Figure 21:
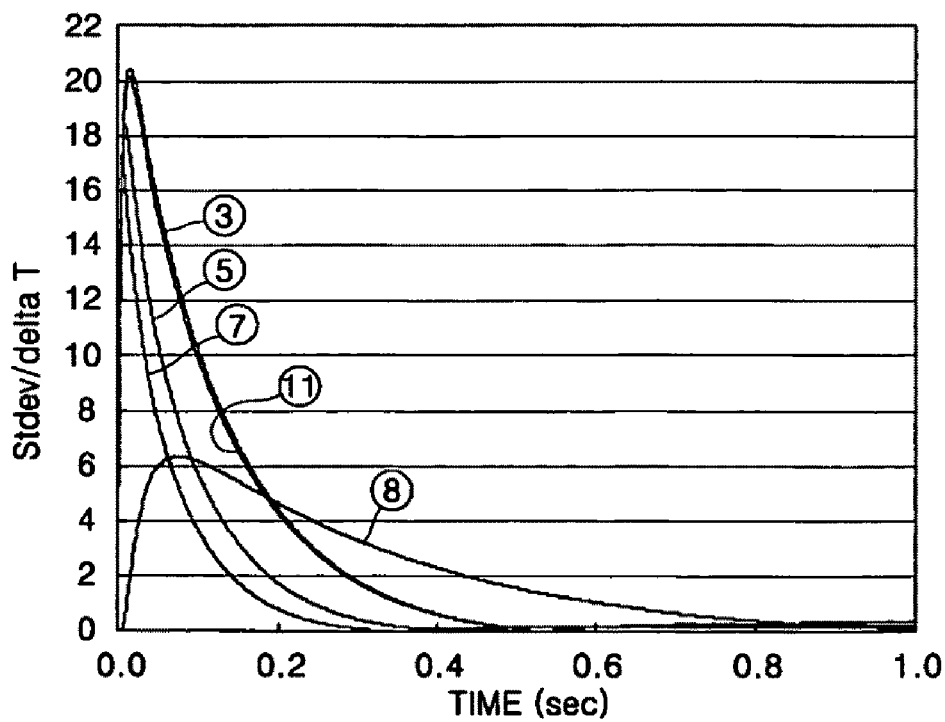
FIG. 21 is a graph that illustrates a ratio of the standard deviation of water temperature of the graph of FIG. 19 with respect to the total temperature change value.

As shown in FIG. 21, a time required for accomplishing temperature uniformity of 2% or less of total temperature change value was 0.5 seconds or less. This means that when a temperature change of 50° C. occurs, a period of time sufficient to accomplish temperature uniformity of 1° C. or less is 0.5 seconds.

Based on the above simulation results, response characteristics with respect to temperature and temperature uniformity are summarized in Table 3 below.

TABLE 3

| Simulation section | Thickness of substrate between channel and heater ($G_P$) | Aspect ratio of channel ($W_C/H_C$) | Ratio of water height to channel height ($H_W/H_C$) | Cooling 90% Target (msec) | Cooling NorStdev = 2% (msec) | Heating 90% Target (msec) | Heating NorStdev = 2% (msec) |
|---|---|---|---|---|---|---|---|
| Three dimensional simulation | 10 μm | 1(100/100) | 0.9 | 287 | 384 | 262 | 703 |
| Two dimensional simulation | 10 μm | 1(100/100) | 0.5 | 320 | 212 | 316 | 238 |
| | | | 0.8 | 271 | 284 | 268 | 325 |
| | | | 0.9 | 239 | 292 | 236 | 337 |
| | | 2(140/70) | 0.8 | 186 | 185 | 184 | 201 |
| | | | 0.9 | 155 | 190 | 154 | 208 |
| | | 4(200/50) | 0.8 | 133 | 142 | 132 | 152 |
| | | | 0.9 | 113 | 143 | 112 | 153 |
| | 100 μm | 1(100/100) | 0.9 | 620 | 440 | 618 | 556 |

The graphs of FIGS. 19 and 20 show both the results of the two- and three-dimensional simulations to compare the two results. In the graphs of FIGS. 19 and 20, ⑪ represents a heating curve of the three-dimensional simulation and ⑫ represents a cooling curve of the three-dimensional simulation.

From the graphs of FIGS. 19 and 20, it can be seen that the results of the three-dimensional simulation are similar to those of the two-dimensional simulations.

Meanwhile, to rapidly perform PCR, oil and water droplet must rapidly reach the temperatures of heaters disposed on a lower surface of a reaction channel. In this regard, when two areas with different temperatures are adjacent to each other, a spatial temperature profile of the inside of a reaction channel was evaluated.

Figure 18:
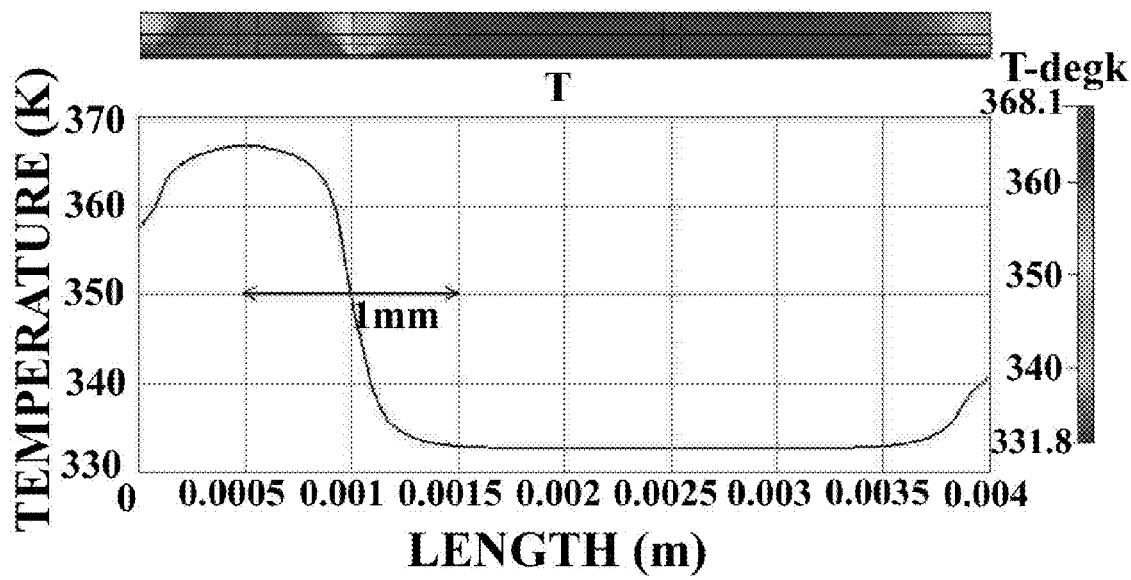
FIG. 18 is a graph that illustrates a temperature profile of the inside of a channel along the longitudinal direction of the channel.

FIG. 18 is a graph that illustrates a temperature profile of the inside of a reaction channel along the longitudinal direction of the reaction channel. In FIG. 18, the length "1 mm" of a left side indicates a 95° C. area and the length "3 mm" of a right side indicates a 60° C. area.

As shown in FIG. 18, a temperature area is influenced by another temperature area within 0.5 mm distance. This means that when a distance between two areas with different temperatures is about 1 mm, the two areas completely get out of the interaction.

Like the above-described two-dimensional simulations, to evaluate temperature uniformity of water droplet surrounded by oil in the three-dimensional simulation, standard deviations of temperatures at 18 spots of the water droplet were calculated.

FIG. 21 is a graph that illustrates a ratio of the standard deviation of water temperature to the total temperature change value in the three-dimensional simulation. The graph of FIG. 21 shows both the results of the two- and three-dimensional simulations to compare the two results. In the graph of FIG. 21, ⑪ represents a three-dimensional simulation curve.

As shown in Table 3, both the response characteristics of temperature and temperature uniformity that are important factors of thermal characteristics reached a desired level within one second. In particular, when a thickness of a substrate made of PDMS between a heater and a reaction channel was 10 μm, a uniform distribution of a target temperature was accomplished within 0.5 seconds.

As apparent from the above description, according to the present invention, a reactant aqueous solution passes through an inlet channel with a constant sectional area at a constant flow rate. Therefore, several tens to several hundreds of aqueous solution droplets surrounded by oil and having fine and uniform sizes can be easily created in a reaction channel or a reaction chamber, which ensures rapid repeated PCR experiments in a relatively small-sized apparatus. Furthermore, since the aqueous solution droplets are surrounded by oil, a contamination problem that may be caused by adsorption of amplification reactants onto the inside of the reaction channel can be prevented and there is no risk of evaporation even when the reactants have a very small volume.

According to the present invention, a reactant aqueous solution, a NTC aqueous solution, and a standard sample aqueous solution are all together introduced into a single reaction channel and then experiments are simultaneously carried out. Therefore, there are advantages in that a PCR apparatus of the present invention can be miniaturized, relative to a conventional PCR apparatus, and a time required for real-time PCR can be remarkably reduced. Furthermore, since a fluorescent signal is emitted from each of the aqueous solution droplets flowing at a predetermined distance in the reaction channel, a quantitative assay of the fluorescent signal can be more simply and accurately performed, relative to a conventional PCR technique in which a fluorescent signal is emitted from the entire surface of a reaction channel. Still furthermore, a real-time PCR curve can be obtained by one-pot image assay in a single apparatus, which enables quantitative assay of nucleic acids.

According to the present invention, the structural change of an inlet channel enables hot-start PCR as well as multiplex PCR for simultaneous assay of multiple genes in a single small-sized apparatus.

A nucleic acid amplification apparatus of the present invention can include a heating unit composed of a plurality of independently controllable heaters. Therefore, a substrate can have differentially programmable temperature areas, which enables nucleic acid amplification experiments under different temperature conditions in a single apparatus.

In addition, according to the present invention, single molecule PCR in which two-step PCR is performed in a single apparatus is possible, thereby enhancing sensitivity of PCR.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method for amplifying nucleic acids, which comprises:
    introducing into a reaction vessel via different inlet channels a reactant aqueous solution containing reactants for nucleic acid amplification and a fluid that is phase-separated from the reactant aqueous solution and does not participate in amplification reaction;
    creating a plurality of reactant aqueous solution droplets surrounded by the fluid by contacting the reactant aqueous solution with the fluid in the reaction vessel; and
    amplifying the nucleic acids in the reactant aqueous solution droplets,
    wherein the reaction vessel comprises two primary reaction channels and a single secondary reaction channel connected to a terminal end of each of the two primary reaction channels, and the operation of introducing the reactant aqueous solution and the fluid into the reaction vessel, the operation of creating the reactant aqueous solution droplets, and the operation of amplifying the nucleic acids are performed in each of the two primary reaction channels, and
    wherein after the operation of amplifying the nucleic acids, the method further comprises:
    combining the reactant aqueous solution droplets in a starting end of the secondary reaction channel to create a plurality of combined reactant aqueous solution droplets in the secondary reaction channel; and
    amplifying the nucleic acids in the combined reactant aqueous solution droplets.

2. The method of claim 1, wherein the fluid is at least one selected from the group consisting of silicon oil, mineral oil, perfluorinated oil, hydrocarbon oil, and vegetable oil.

3. The method of claim 1, wherein the operation of amplifying the nucleic acids is performed by one selected from the group consisting of polymerase chain reaction (PCR), ligase chain reaction (LCR), strand-displacement amplification (SDA), nucleic acid sequence-based amplification (NASBA), transcription-mediated amplification (TMA), and loop-mediated isothermal amplification (LAMP).

4. The method of claim 3, wherein the operation of amplifying the nucleic acids is performed by PCR.

5. The method of claim 4, wherein the operation of amplifying the nucleic acids is performed by continuous-flow PCR in which a substrate is heated to have at least two different temperature areas and the reactant aqueous solution droplets alternately and repeatedly pass through the different temperature areas.

6. The method of claim 5, wherein the substrate is heated to have at least two different temperature areas using a plurality of independently controllable heaters.

7. The method of claim 4, wherein the operation of introducing the reactant aqueous solution and the fluid into the reaction vessel further comprises introducing into the reaction vessel at least one aqueous solution of a negative control and a positive control for quantitative assay and a standard sample aqueous solution via respective inlet channels, different from the inlet channels for the introduction of the reactant aqueous solution and the fluid, and
    the operation of creating the reactant aqueous solution droplets further comprises creating a plurality of control aqueous solution droplets and a plurality of standard sample aqueous solution droplets by contacting the at least one aqueous solution of the negative control and the positive control and the standard sample aqueous solution with the fluid in the reaction vessel.

8. The method of claim 7, wherein in the operation of introducing the reactant aqueous solution and the fluid into the reaction vessel, the standard sample aqueous solution is adjusted to at least two concentrations and then introduced into the reaction vessel.

9. The method of claim 4, wherein in the operation of introducing the reactant aqueous solution and the fluid into the reaction vessel, at least two reactant aqueous solutions containing at least two primers are introduced into the reaction vessel via respective inlet channels.

10. The method of claim 4, wherein in the operation of introducing the reactant aqueous solution and the fluid into the reaction vessel, a nucleic acid aqueous solution, a common component containing polymerase and dNTP, and a primer are introduced into respective inlet channels and mixed before being introduced into the reaction vessel to form the reactant aqueous solution.

* * * * *